US008744552B2

(12) United States Patent
Akuzawa et al.

(10) Patent No.: US 8,744,552 B2
(45) Date of Patent: Jun. 3, 2014

(54) BIOPSY APPARATUS

(75) Inventors: Hayato Akuzawa, Kanagawa-ken (JP); Hajime Nakata, Kanagawa-ken (JP); Yousuke Tsukamizu, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 541 days.

(21) Appl. No.: 12/926,406

(22) Filed: Nov. 16, 2010

(65) Prior Publication Data

US 2011/0118625 A1      May 19, 2011

(30) Foreign Application Priority Data

Nov. 17, 2009   (JP) .................................. 2009-262279

(51) Int. Cl.
  *A61B 10/00*   (2006.01)
  *A61B 19/00*   (2006.01)
  *A61B 5/05*    (2006.01)

(52) U.S. Cl.
  USPC ........... 600/424; 600/562; 600/564; 600/568; 606/130

(58) Field of Classification Search
  USPC .................................. 600/562–572; 606/130
  See application file for complete search history.

(56) References Cited

U.S. PATENT DOCUMENTS

| 4,727,565 A |   | 2/1988  | Ericson |
| 5,078,142 A |   | 1/1992  | Siczek et al. |
| 5,386,447 A |   | 1/1995  | Siczek |
| 5,594,769 A | * | 1/1997  | Pellegrino et al. ............. 378/37 |
| 5,833,627 A |   | 11/1998 | Shmulewitz et al. |
| 6,022,325 A | * | 2/2000  | Siczek et al. .................. 600/568 |
| 7,769,426 B2 |   | 8/2010  | Hibner et al. |
| 2005/0004580 A1 | * | 1/2005 | Jokiniemi et al. ............ 606/130 |
| 2008/0103387 A1 |   | 5/2008 | Gross |
| 2009/0171244 A1 | * | 7/2009 | Ning et al. ..................... 600/567 |

FOREIGN PATENT DOCUMENTS

| EP | 0288187       | 10/1988 |
| JP | 1-256942      | 10/1989 |
| JP | 7-504586      | 5/1995  |
| JP | 11-505446     | 5/1999  |
| JP | 2004-033753   | 2/2004  |
| JP | 2008-513090   | 5/2008  |
| WO | WO 93/17620   | 9/1993  |

OTHER PUBLICATIONS

Rejection of the Application issued by JPO on Oct. 29, 2013 in connection with corresponding Japanese Patent Application No. 2009-262279.
Decision to Dismiss the Amendment issued by the Japanese Patent Office (JPO) on Feb. 4, 2014 in connection with JP2009-262279.
Decision of Rejection issued by the Japanese Patent Office (JPO) on Feb. 4, 2014 in connection with JP2009-262279.

* cited by examiner

*Primary Examiner* — Brian Szmal
*Assistant Examiner* — Megan Leedy
(74) *Attorney, Agent, or Firm* — Jean C. Edwards, Esq.; Edwards Neils PLLC

(57) ABSTRACT

A biopsy apparatus includes a biopsy region positional information calculator for calculating a three-dimensional position of a biopsy region, a biopsy needle moving mechanism for moving a biopsy needle along three axes and/or turning the biopsy needle obliquely to an object to be examined, a biopsy needle positional information calculator for calculating a three-dimensional position of the biopsy needle, and a traveled distance calculator for calculating a distance over which the biopsy needle moves with respect to the biopsy region based on the three-dimensional position of the biopsy needle and the three-dimensional position of the biopsy region.

10 Claims, 21 Drawing Sheets

BIOPSY APPARATUS

CROSS-REFERENCE TO RELATED APPLICATION

This application is based upon and claims the benefit of priority from Japanese Patent Application No. 2009-262279 filed on Nov. 17, 2009, of which the contents are incorporated herein by reference.

BACKGROUND OF THE INVENTION

1. Field of the Invention

The present invention relates to a biopsy apparatus, which is incorporated in a radiographic image capturing apparatus for capturing radiographic images of an object to be examined, and which operates by inserting a biopsy needle into a biopsy region of an object to be examined and sampling tissue from the biopsy region.

2. Description of the Related Art

There have heretofore been developed biopsy apparatus for sampling tissue of a biopsy region in an object to be examined of a subject and thoroughly examining the sampled tissue to perform a disease diagnosis. Such a biopsy apparatus often is incorporated in a radiographic image capturing apparatus. The radiographic image capturing apparatus applies radiation to an object to be examined in different directions in order to capture a plurality of radiographic images of a biopsy region in a stereographic image capturing process. The biopsy apparatus determines the three-dimensional position of the biopsy region from the acquired radiographic images, moves a biopsy needle to the biopsy region based on the determined three-dimensional position, and samples tissue from the biopsy region with the biopsy needle.

It is assumed that when tissue is sampled from a biopsy region in a subject's breast as the object to be examined, the breast is placed on an image capturing base, which houses therein a radiation detector for converting radiation into a radiographic image. The breast is compressed against the image capturing base by a compression plate, which is displaced toward the image capturing base.

The biopsy apparatus samples tissue from the biopsy region in the breast by inserting the biopsy needle into the breast through an opening defined in the compression plate. In the art, there are different processes for inserting the biopsy needle into the breast. They include (1) a process for inserting the biopsy needle into the breast along a direction in which the compression plate compresses the breast (in the description of the related art, this process will be referred to as "vertical piercing") and (2) a process for inserting the biopsy needle into the breast while the biopsy needle is oriented obliquely to the direction in which the compression plate compresses the breast (in the description of the related art, this process will be referred to as "oblique piercing"). Commercially available biopsy apparatus, which are presently available in the market, sample tissue from a biopsy region according to either one of the processes (1) or (2). The biopsy needle has a sampler for sampling tissue under suction, at a position that is slightly offset from the tip end thereof toward the proximal end thereof.

A biopsy apparatus that operates according to the vertical piercing process is capable of sampling tissue from a biopsy region in a breast that is relatively thick. However, when the sampler of the biopsy needle is aligned with a biopsy region in a relatively thin breast and the biopsy needle is inserted into the biopsy region, the tip end of the biopsy needle tends to pierce through the relatively thin breast (see FIG. 13C of the accompanying drawings). According to the vertical piercing process, therefore, it is difficult to sample tissue from a region of a relatively thin breast, which is close to the image capturing base. In addition, the vertical piercing process fails to quickly sample breast tissue that is spread in a planar direction along the compression plate or the image capturing base.

The biopsy apparatus that operates according to the oblique piercing process is capable of sampling tissue from a region of a relatively thin breast, which is close to the image capturing base, because the biopsy needle is inserted obliquely into the breast. However, since the biopsy needle is inserted obliquely into the breast, the breast includes a dead zone (shown by hatching in FIGS. 13A and 13B of the accompanying drawings) from which tissue cannot be sampled, positioned below an outer circumferential area of the opening in the compression plate, regardless of the thickness of the breast. In order to sample tissue from the dead zone, it is necessary to release the breast from the compression plate, then position the breast so that the dead zone is placed at the center of the opening as viewed in plan, compress the breast again with the compression plate, and insert the biopsy needle obliquely into the breast. Therefore, in the oblique piercing process, it is necessary to repeat a sequence of successive steps of positioning the breast, compressing the breast, capturing an image of the breast, inserting the biopsy needle into the breast, sampling tissue from the breast, and releasing the breast, as many times as the number of tissues to be sampled from the dead zone. As a result, the subject is subjected to the examination procedure for a long period of time, and is exposed to an increased dose of radiation.

The vertical piercing process and the oblique piercing process are disclosed respectively in Japanese Laid-Open Patent Publication No. 01-256942, Japanese Laid-Open Patent Publication No. 07-504586 (PCT), Japanese Laid-Open Patent Publication No. 11-505446 (PCT), Japanese Laid-Open Patent Publication No. 2004-033753, and Japanese Laid-Open Patent Publication No. 2008-513090 (PCT), for example.

Because such conventional biopsy apparatus sample tissue from a biopsy region according to either one of the vertical piercing process or the oblique piercing process, as described above, such apparatus fail to sample tissue reliably and efficiently.

SUMMARY OF THE INVENTION

It is an object of the present invention to provide a biopsy apparatus, which is capable of reliably and efficiently sampling tissue from a biopsy region in an object to be examined, regardless of the thickness of the object to be examined, so that tissue can be sampled in a reduced period of time, and so that the subject is exposed to a reduced dose of radiation.

To achieve the above object, there is provided in accordance with the present invention a biopsy apparatus for use in a radiographic image capturing apparatus having a radiation source for applying radiation to an object to be examined, and a radiation detector for detecting radiation that has passed through the object to be examined and converting the detected radiation into a radiographic image, the biopsy apparatus being arranged so as to insert a biopsy needle into a biopsy region of the object to be examined and sample tissue from the biopsy region, the biopsy apparatus comprising a biopsy region positional information calculator for calculating a three-dimensional position of the biopsy region based on at least two radiographic images acquired from the radiation detector when radiation is applied in different directions to the object to be examined from the radiation source, a biopsy needle moving mechanism for moving the biopsy needle along three mutually perpendicular axes and/or turning the biopsy needle obliquely with respect to the object to be examined, a biopsy needle positional information calculator for calculating a three-dimensional position of the biopsy needle, and a traveled distance calculator for calculating a distance over which the biopsy needle moves with respect to the biopsy region based on the three-dimensional position of the biopsy needle and the three-dimensional position of the biopsy region, wherein when the biopsy needle moving mechanism turns the biopsy needle, the biopsy needle positional information calculator calculates the three-dimensional position of the biopsy needle based on a turning angle of the biopsy needle.

The biopsy apparatus moves the biopsy needle along three axes and/or turns the biopsy needle obliquely to the object to be examined based on the distance by which the biopsy needle moves with respect to the biopsy region. Accordingly, it is possible to sample tissue from the biopsy region according to an appropriate piercing process depending on the thickness of the breast.

More specifically, if the object to be examined is relatively thick, then tissue may be sampled from the biopsy region according to a piercing process (vertical piercing process) for moving the biopsy needle along three axes. If the object to be examined is relatively thin, then tissue may be sampled from the biopsy region according to a piercing process (oblique piercing process) for turning the biopsy needle obliquely with respect to the object to be examined.

Since the biopsy needle is moved and/or turned in a manner that takes advantage of either the vertical piercing process or the oblique piercing process to sample tissue from the biopsy region, tissue can be sampled reliably and efficiently from the biopsy region regardless of the thickness of the breast. Because the vertical piercing process or the oblique piercing process is selected depending on characteristics of the breast 22, it is possible to prevent dead zones from occurring in the object to be examined.

According to the present invention, furthermore, when the biopsy needle is turned, the three-dimensional position of the tip end of the biopsy needle is calculated based on the turning angle of the biopsy needle. Therefore, the biopsy needle positional information calculator does not require both an algorithm for calculating the three-dimensional position of the biopsy needle when the biopsy needle is not turned as well as an algorithm for calculating the three-dimensional position of the biopsy needle when the biopsy needle is turned, but only requires an algorithm for calculating the three-dimensional position of the biopsy needle when the biopsy needle is turned. Accordingly, the load imposed on and the storage capacity required by the biopsy needle positional information calculator in calculating the three-dimensional position of the biopsy needle is reduced. As a result, time required to calculate the three-dimensional position of the biopsy needle is shortened, and the cost of the biopsy apparatus is lowered.

Since tissue can reliably and efficiently be sampled from the biopsy region regardless of the thickness of the object to be examined, time required to sample tissue from the biopsy region is reduced, and the dosage of radiation applied to the subject can be lowered.

The biopsy needle moving mechanism comprises a biopsy needle holder for holding the biopsy needle, at least two moving units for moving the biopsy needle holder along three axes, a turning unit for turning the biopsy needle holder obliquely with respect to the object to be examined, at least three displacement detectors for detecting displacements respectively along three axes of the biopsy needle holder that is moved by the moving units and outputting the detected displacements to the biopsy needle positional information calculator, and an angle detector for detecting an angular displacement of the biopsy needle holder that is turned by the turning unit and outputting the detected angular displacement to the biopsy needle positional information calculator, wherein the biopsy needle positional information calculator calculates a three-dimensional position of the biopsy needle before being on the detected displacements, and calculates a three-dimensional position of the biopsy needle after being turned based on the angular displacement.

Therefore, the biopsy needle and the biopsy needle holder can reliably and efficiently be turned and moved along three axes, and angular displacement and displacements along three axes can reliably be detected and output to the biopsy needle positional information calculator. Thus, the biopsy needle positional information calculator can accurately calculate the three-dimensional position of the biopsy needle.

The biopsy needle moving mechanism further comprises a base that is placed on the radiographic image capturing apparatus when the biopsy needle moving mechanism is incorporated in the radiographic image capturing apparatus, wherein the turning unit turns the biopsy needle moving mechanism as a whole with respect to the base, thereby turning the biopsy needle holder.

The biopsy needle moving mechanism is turned as a whole with respect to the base in order to turn the biopsy needle holder. Therefore, the biopsy needle holder does not require a component, e.g., a motor, for turning the biopsy needle. The biopsy needle holder therefore is reduced in size and weight, and hence the mammographic apparatus also is reduced in size and weight.

The biopsy needle moving mechanism may further comprise a reference position changer for changing a reference position for the biopsy needle when the biopsy needle holder holds the biopsy needle.

The biopsy apparatus may further comprise a biopsy needle support for supporting the biopsy needle thereon, the biopsy needle support being held by the biopsy needle holder. While the biopsy needle support is held by the biopsy needle holder, the reference position changer may change the reference position by changing the position of the biopsy needle support with respect to the biopsy needle holder, or by replacing the biopsy needle support, which is currently held by the biopsy needle holder, with another biopsy needle support that is held at a different position by the biopsy needle holder.

When the biopsy needle, the biopsy needle support, and the biopsy needle holder are turned, the distance between the biopsy region and the biopsy needle may be increased. However, such an increase in distance between the biopsy region and the biopsy needle may be canceled, and hence the biopsy apparatus is prevented from becoming increased in size.

The traveled distance calculator may calculate an actual distance over which the biopsy needle moving mechanism has moved and/or turned the biopsy needle holder based on the distance which is output to the biopsy needle moving mechanism. If the traveled distance calculator makes a judgment indicating that the biopsy needle moving mechanism has not moved and/or turned the biopsy needle holder based on the distance output to the biopsy needle moving mechanism, based on the difference between the distance output to the biopsy needle moving mechanism and the actual distance calculated by the traveled distance calculator, the traveled distance calculator may output the judgment to an external circuit.

Since it is easy to recognize whether the biopsy needle moving mechanism currently is moving the biopsy needle or not based on the traveled distance, which is output from the traveled distance calculator, a doctor or radiological technician in charge of the biopsy apparatus can quickly take actions, such as shutting down the biopsy apparatus, when such a judgment (warning) is indicated.

The biopsy needle moving mechanism may further comprise an attachment by which the biopsy needle moving mechanism is removably attached to the radiographic image capturing apparatus.

Consequently, the biopsy apparatus can easily be incorporated in an existing mammographic apparatus.

The object to be examined may comprise a subject's breast, and the radiographic image capturing apparatus may comprise a mammographic apparatus having an image capturing base for containing the radiation detector therein and holding the breast thereon and a compression plate displaceable toward the image capturing base for compressing the breast. The three axes may represent a direction in which the compression plate compresses the breast, and two axial directions perpendicular to the direction in which the compression plate compresses the breast. When the radiation source moves along a plane that extends transversely across a chest wall of the subject and along the direction in which the compression plate compresses the breast, and thereafter applies radiation to the breast, the biopsy needle holder may be turned along a plane that lies along the direction in which the compression plate compresses the breast and across a plane in which the radiation source moves.

Inasmuch as the vertical piercing process or the oblique piercing process is used to sample tissue from the biopsy region depending on the thickness of the subject's breast, tissue can reliably and efficiently be sampled from the biopsy region in the breast. As a result, the time required to sample tissue from the biopsy region and the dosage of radiation applied to the subject are reduced.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
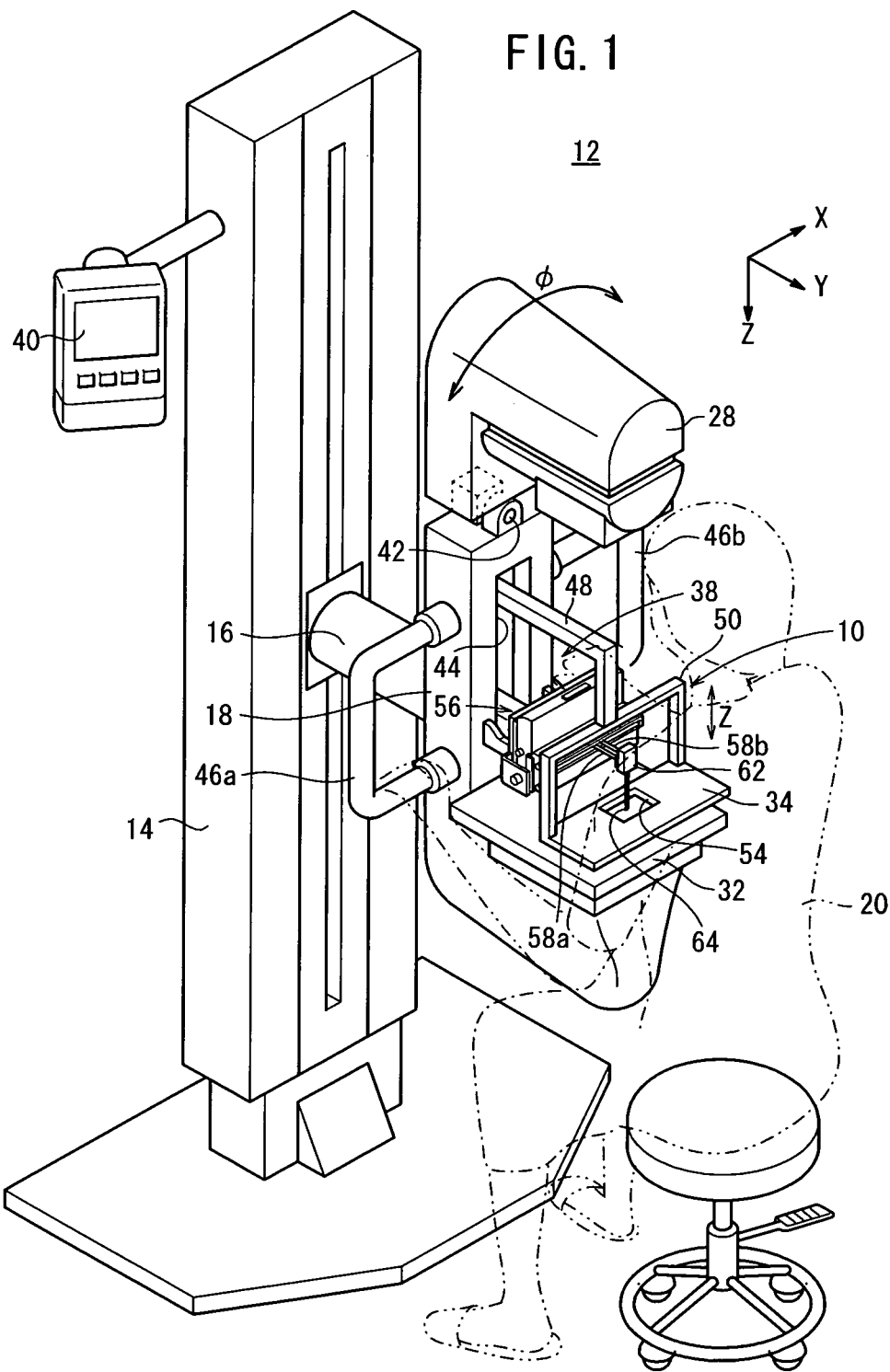
FIG. 1 is a perspective view of a mammographic apparatus incorporating a biopsy apparatus therein according to an embodiment of the present invention.

A mammographic apparatus according to a preferred embodiment of the present invention will be described in detail below with reference to FIGS. 1 through 21B.

The basic structure of the mammographic apparatus (radiographic image capturing apparatus) 12 according to an embodiment of the present invention, and which incorporates a biopsy apparatus 10 therein, will be described below with reference to FIGS. 1 and 2.

The mammographic apparatus 12 basically includes an upstanding base 14, a vertical arm 18 fixed to the distal end of a swing shaft 16 disposed substantially centrally on the base 14, a radiation source housing unit 28 housing therein a radiation source 26 for applying radiation 24 to a breast 22 as an object to be examined of an examinee (subject) 20 and which is fixed to an upper end of the arm 18, an image capturing base 32 mounted on a lower end of the arm 18 and housing therein a solid-state detector (radiation detector) 30 for detecting radiation 24 that has passed through the breast 22, a compression plate 34 for compressing and holding the breast 22 against the image capturing base 32, and a biopsy hand assembly 38 for removing a tissue sample from a biopsy region 36 in the breast 22, the biopsy hand assembly 38 being mounted on the arm 18 over the image capturing base 32.

Figure 2:
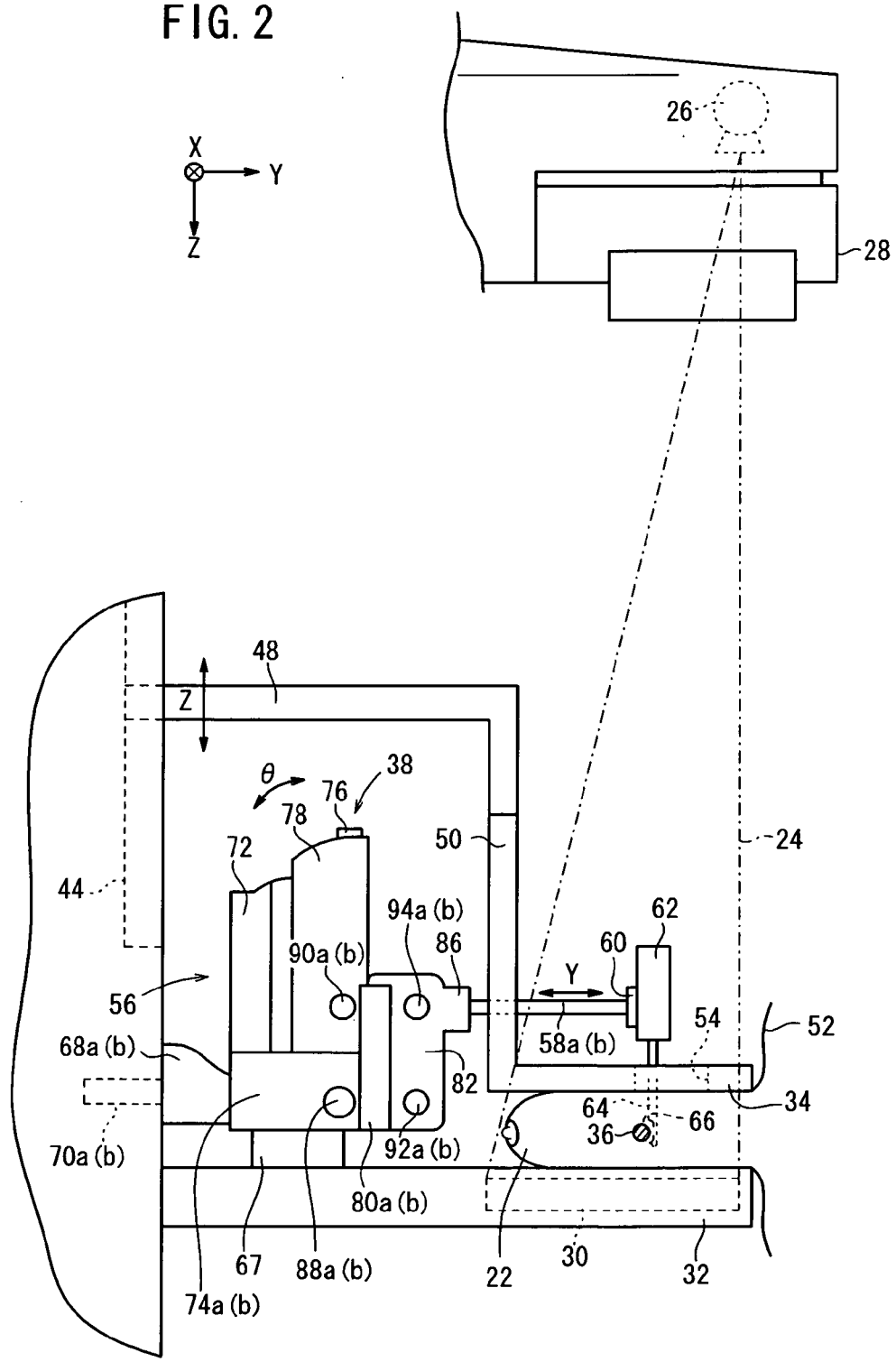
FIG. 2 is an enlarged fragmentary side elevational view of the mammographic apparatus shown in FIG. 1.

In FIGS. 1 and 2, the mammographic apparatus 12 applies radiation 24 to the breast 22 of the examinee 20 in order to capture a radiographic image, and the biopsy apparatus 10 removes a sample tissue from the biopsy region 36 while the breast 22 of the examinee 20, who is in a sitting position, is compressed and secured between the compression plate 34 and the image capturing base 32. To the base 14, there is connected a display control panel 40 for displaying image capturing conditions representing an image capturing region of the examinee 20, ID information of the examinee 20, etc., and setting such items of information as necessary.

When the arm 18, to which the radiation source housing unit 28 and the image capturing base 32 are secured, is moved angularly about the swing shaft 16, the direction of the radiation source housing unit 28 and the image capturing base 32 with respect to the breast 22 of the examinee 20 is adjusted. The radiation source housing unit 28 is operatively coupled to the arm 18 by a hinge 42. The radiation source housing unit 28 can be turned about the hinge 42 in directions indicated by the arrow φ independently of the image capturing base 32.

The arm 18 has a groove 44 defined vertically in a side (front side) thereof, which faces toward the examinee 20 in the direction indicated by the arrow Y. The groove 44 extends along the direction indicated by the arrow Z. Handles 46a, 46b are mounted on respective sides of the arm 18, which face away from each other in the direction indicated by the arrow Y. The handles 46a, 46b are gripped by the examinee 20. A compression plate attachment 48, which extends in the direction indicated by the arrow Y, has a proximal end inserted into the groove 44 and held in interfitting engagement with a mount (not shown) disposed in the arm 18. The compression plate attachment 48 has a distal end portion, which is bent in the direction indicated by the arrow Z and connected to a U-shaped compression plate connector 50, which has distal ends thereof coupled to a side of the compression plate 34 that is located more closely to the arm 18.

With the proximal end of the compression plate attachment 48 being held in interfitting engagement with the mount, the compression plate 34 is kept at a certain height between the radiation source housing unit 28 and the image capturing base 32. When the mount is displaced in and along the groove 44 in directions indicated by the arrow Z, the compression plate 34 is displaced in unison with the mount in directions indicated by the arrow Z. The compression plate 34 has an opening 54 defined in a portion thereof that is closer to the chest wall 52 (see FIG. 2) of the examinee 20. The opening 54 allows the biopsy hand assembly 38 to sample tissue from the biopsy region 36 in the breast 22.

The biopsy hand assembly 38 comprises a biopsy needle moving mechanism 56, which is mounted on the image capturing base 32 closely to the arm 18, and a biopsy needle 64 movable by the biopsy needle moving mechanism 56 along three axes, i.e., along directions indicated by the arrows X, Y, Z, and/or which is swingable along directions indicated by the arrow θ obliquely to the breast 22. A plate-shaped biopsy needle holder 60 is attached to distal ends of rods 58a, 58b, which extend from and are movable toward and away from the biopsy needle moving mechanism 56 in directions indicated by the arrow Y. The biopsy needle 64 is mounted on a biopsy needle support 62 that is attached to the biopsy needle holder 60.

As shown in FIG. 2, the directions indicated by the arrow θ, along which the biopsy needle 64 is swingable, extend in a Y-Z plane. As shown in FIG. 1, the directions indicated by the arrow φ, along which the radiation source housing unit 28 is angularly movable, extend in an X-Z plane. The Y-Z plane and the X-Z plane lie perpendicularly to each other.

The U-shaped compression plate connector 50 and the compression plate 34, which are coupled jointly to each other, define an opening extending along the X-Z plane (see FIG. 1). The biopsy needle moving mechanism 56, which is mounted on the image capturing base 32, moves the rods 58a, 58b and the biopsy needle holder 60 through the opening toward and away from the chest wall 52 of the examinee 20.

The biopsy needle support 62 on which the biopsy needle 64 is mounted is attached to the biopsy needle holder 60 by a doctor or radiological technician in charge of the mammographic apparatus 12, such that the biopsy needle holder 60 is located at a position between the opening and the chest wall 52, i.e., at a position out of physical interference with the radiation source housing unit 28 and the chest wall 52.

Alternatively, the biopsy needle support 62 may be attached to the biopsy needle holder 60 beforehand, or at a time when the biopsy needle moving mechanism 56 is incorporated in the mammographic apparatus 12. In this case, when the biopsy needle moving mechanism 56 is actuated, the biopsy needle support 62 and the biopsy needle 64 move through the opening toward the chest wall 52.

The biopsy needle 64 has a sampler 66 located near the lower end thereof for sampling under suction tissue (e.g., calcified tissue) from the biopsy region 36, which forms a lesion area (e.g., calcified area) in the breast 22. The sampler 66 of the biopsy needle 64 can be moved to a position in the vicinity of the biopsy region 36 when the biopsy needle moving mechanism 56 moves the biopsy needle holder 60, the biopsy needle support 62, and the biopsy needle 64 together in the X-Y plane parallel to the surface of the compression plate 34 and along directions indicated by the arrow Z, and/or turns the biopsy needle holder 60, the biopsy needle support 62, and the biopsy needle 64 along directions indicated by the arrow θ.

Structural details of the biopsy needle moving mechanism 56 will be described below with reference to FIGS. 2 through 10.

Figure 3:
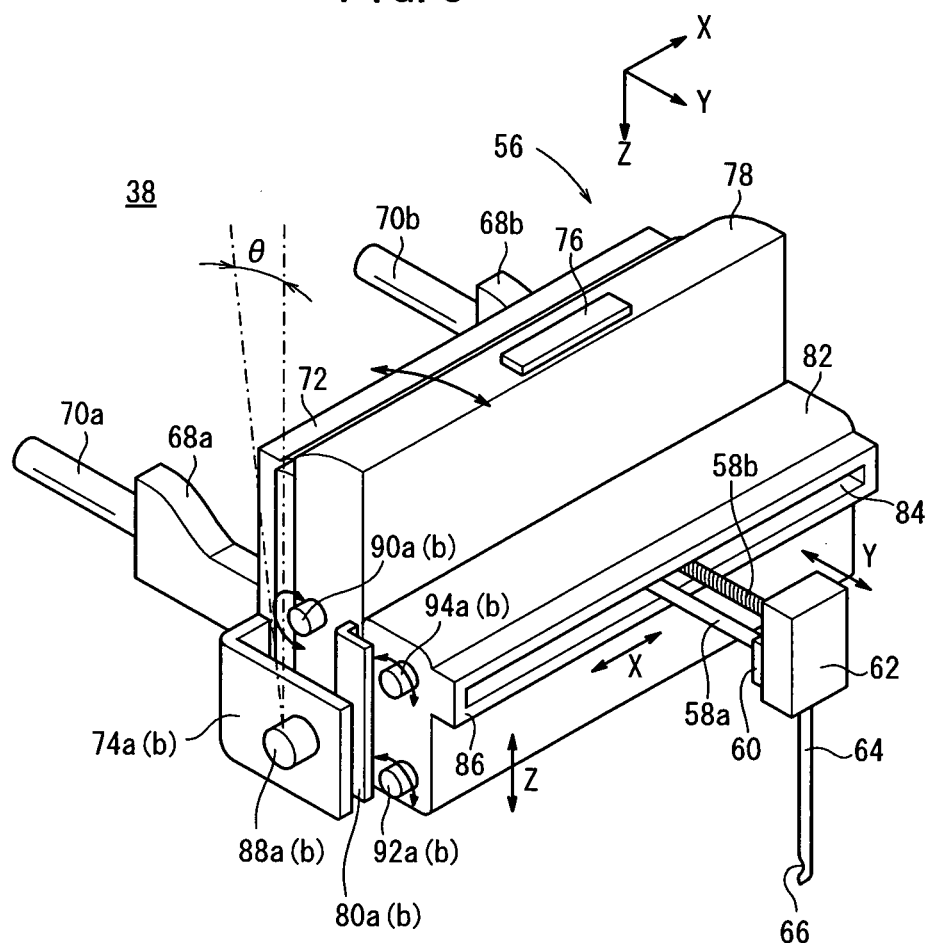
FIG. 3 is a perspective view of a biopsy needle moving mechanism of the mammographic apparatus shown in FIG. 1.

First, the appearance of the biopsy needle moving mechanism 56 will be described below with reference to FIGS. 2 and 3. The biopsy needle moving mechanism 56 is horizontally symmetrical in structure with respect to the Z-axis, as viewed in a direction from the examinee 20 toward the arm 18.

More specifically, the biopsy needle moving mechanism 56, which is mounted via a base 67 on the image capturing base 32, comprises a pair of positioning members (attachments) 68a, 68b disposed on a rear surface facing the arm 18 for abutment against the arm 18, and a pair of rods (attachments) 70a, 70b extending respectively from the positioning members 68a, 68b toward the arm 18. The positioning members 68a, 68b and the rods 70a, 70b extend along directions indicated by the arrow Y. When the base 67 is held in contact with the image capturing base 32, the rods 70a, 70b are inserted into respective recesses defined in the arm 18 until the positioning members 68a, 68b abut against the arm 18, whereupon the biopsy needle moving mechanism 56 is positioned and fixed in the mammographic apparatus 12, as shown in FIGS. 1 and 2.

A rear face member 72 is attached vertically to the rear surface of the biopsy needle moving mechanism 56, which faces toward the arm 18. The rear face member 72 is coupled to the positioning members 68a, 68b and the base 67. Curved members 74a, 74b, which are partially bent in the direction indicated by the arrow Y, are connected to respective opposite sides of the rear face member 72 in directions indicated by the arrow X. The rear face member 72 has an upper surface that faces the examinee 20, and which is curved along directions indicated by the arrow θ.

A lever 76 is fixed to the surface of the rear face member 72, which faces toward the examinee 20. A turning unit 78, which is capable of turning along directions indicated by the arrow θ, also is mounted on the surface of the rear face member 72. Curved members 80a, 80b, which are partially bent in the direction indicated by the arrow Y, are disposed on respective opposite sides of the turning unit 78 in directions indicated by the arrow X. A moving unit 82, which is capable of moving along directions indicated by the arrow Z, is mounted on a surface of the turning unit 78 that faces in the direction indicated by the arrow Y.

A moving unit 86 serves to move the rods 58a, 58b, the biopsy needle holder 60, the biopsy needle support 62, and the biopsy needle 64 together in directions indicated by the arrow X along a groove 84 defined therein along directions indicated by the arrow X. The moving unit 86 projects from a surface of the moving unit 82 toward the examinee 20 in the direction indicated by the arrow Y.

Shafts 88a, 88b are mounted respectively on the curved members 74a, 74b, and handles 90a, 90b are mounted respectively on both sides of the turning unit 78. Handles 92a, 94a and handles 92b, 94b are mounted respectively on both sides of the moving unit 82.

The appearance of the biopsy needle moving mechanism 56 has been described above. Internal structural details of the biopsy needle moving mechanism 56 will be described below with reference to FIGS. 4 through 10. In each of FIGS. 4 through 10, only a portion of the internal structural details of the biopsy needle moving mechanism 56 is illustrated.

First, among the internal structural details of the biopsy needle moving mechanism 56, structural details of a structure for producing turning movement in directions indicated by the arrow θ will be described below with reference to FIGS. 4 and 5.

Figure 4:
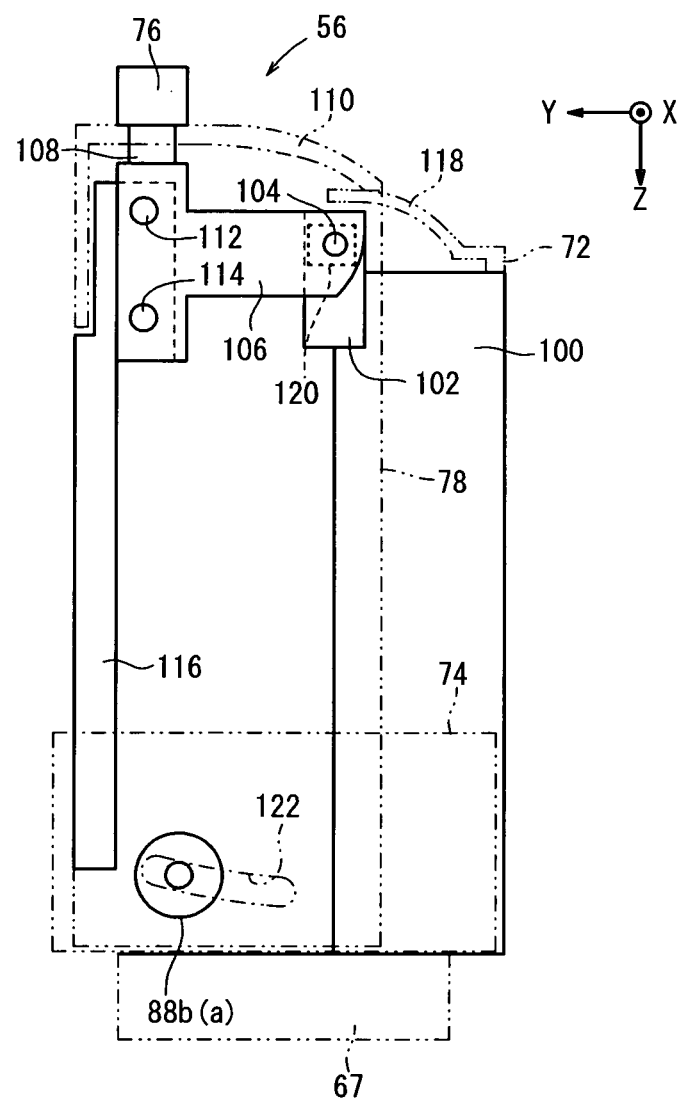
FIG. 4 is a side elevational view illustrating internal structural details of the biopsy needle moving mechanism shown in FIG. 3.

As shown in FIG. 4, the biopsy needle moving mechanism 56 comprises an upstanding support member 100 connected to the base 67 and the rear face member 72. The upstanding support member 100 supports on an upper portion thereof another support member 102, on which an L-shaped turning member 106 is supported pivotally by a shaft 104 such as a rod or the like. The lever 76 is coupled to the turning member 106 by a joint 108, which extends through an upper wall 110 of the turning unit 78. A plate 116 is fixed to a side of the turning member 106, which faces in the direction indicated by the arrow Y, by fixing members 112, 114 such as fasteners or the like.

The upper wall 110 of the turning unit 78 is curved along directions indicated by the arrow θ. The rear face member 72 has an upper wall 118 held against the upper wall 110 of the turning unit 78. The upper wall 118 also is curved along directions indicated by the arrow θ. A rotary encoder (angle detector) 120 is connected to the shaft 104. The shafts 88a, 88b have respective distal ends that extend into the turning unit 78 through the curved members 74a, 74b and side walls of the turning unit 78. The side walls of the turning unit 78 have respective arcuate grooves 122 defined therein, which receive the distal ends of the shafts 88a, 88b.

The curved members 80a, 80b and the moving unit 82 are mounted on the turning unit 78. The moving unit 86 is mounted on the moving unit 82. The moving unit 86 serves to move the rods 58a, 58b, the biopsy needle holder 60, the biopsy needle support 62, and the biopsy needle 64 together in directions indicated by the arrow X.

When a doctor or radiological technician pulls the lever 76 in one of the directions indicated by the arrow θ (see FIGS. 2 and 3) shown in FIG. 4, the turning member 106 is turned about the shaft 104 with respect to the support member 102, thereby turning the turning unit 78 including the joint 108 connected to the turning member 106 and the lever 76, the curved members 80a, 80b and the moving unit 82 mounted on the turning unit 78, the moving unit 86 mounted on the moving unit 82, and the rods 58a, 58b, the biopsy needle holder 60, the biopsy needle support 62, and the biopsy needle 64, which are mounted on the moving unit 86, in unison with each other along the same direction indicated by the arrow θ.

The grooves 122 are curved arcuately along directions indicated by the arrow θ. Therefore, when a doctor or radiological technician pulls the lever 76, the relative position of the grooves 122 with respect to the shafts 88a, 88b changes, thereby causing components of the biopsy needle moving mechanism 56, except for the base 67, the rear face member 72, the support members 100, 102, and the shafts 88a, 88b, to turn in unison with each other along directions indicated by the arrow θ (see FIG. 5).

With the components shown in FIG. 4 included in or mounted on the turning unit 78, consequently, the biopsy needle moving mechanism 56 is turned as a whole along directions indicated by the arrow θ when the turning unit 78 is turned along directions indicated by the arrow θ.

The rotary encoder 120 detects, as a turning angle θ, an angular displacement of the turning member 106 with respect to the support member 102, and outputs the detected turning angle θ to an external circuit.

Among the internal structural details of the biopsy needle moving mechanism 56, structural details of a structure for producing movement in directions indicated by the arrow Z will be described below with reference to FIGS. 6 and 7.

A motor 132 and a rotary encoder (displacement detector) 134 are mounted by a mount plate 130 on a portion of the plate 116 (see FIGS. 5 through 7), which faces in the direction indicated by the arrow Z, i.e., toward the base 67. The motor 132 has a rotational shaft 136 with a gear 138 mounted thereon. The gear 138 is held in mesh with a gear 142 that is mounted on a rod 140, opposite ends of which are connected respectively to the handles 90a, 90b.

The rod 140 is rotatably supported by and extends through bearings 144a, 144b, which are disposed inwardly of the side walls of the turning unit 78. The rod 140 also extends through the side walls of the turning unit 78 and has opposite ends thereof connected to the respective handles 90a, 90b. Worms 146a, 146b are supported respectively on the rod 140 near the bearings 144a, 144b. The plate 116 has holes 148a, 148b defined respectively therein near the worms 146a, 146b. The worms 146a, 146b are held in mesh with respective worm wheels 152a, 152b, which are mounted on respective distal ends of rods 150a, 150b that extend respectively through the holes 148a, 148b.

The moving unit 82 houses therein a plate 156, which is spaced from the plate 116 in the direction indicated by the arrow Y, and which extends in parallel to the plate 116. The plate 156 supports racks 158a, 158b on a surface thereof that faces the plate 116, the racks 158a, 158b extending along directions indicated by the arrow Z. The racks 158a, 158b are held in mesh with respective pinions 154a, 154b mounted respectively on other ends of the rods 150a, 150b.

When the motor 132 is energized to rotate the rotational shaft 136 about its axis, the rod 140 also is rotated by the gears 138, 142 about its axis. The worm wheels 152a, 152b, which are held in mesh with the worms 146a, 146b, convert rotation of the rod 140 about the axis thereof, i.e., about directions indicated by the arrow X, into rotation about directions indicated by the arrow Y, thereby rotating the rods 150a, 150b about respective axes thereof. The racks 158a, 158b, which are held in mesh with the pinions 154a, 154b on the rods 150a, 150b, convert rotation of the rods 150a, 150b about axes thereof into linear movement along directions indicated by the arrow Z. As a result, the plate 156, on which the racks 158a, 158b are mounted, also is moved along directions indicated by the arrow Z.

Figure 7:
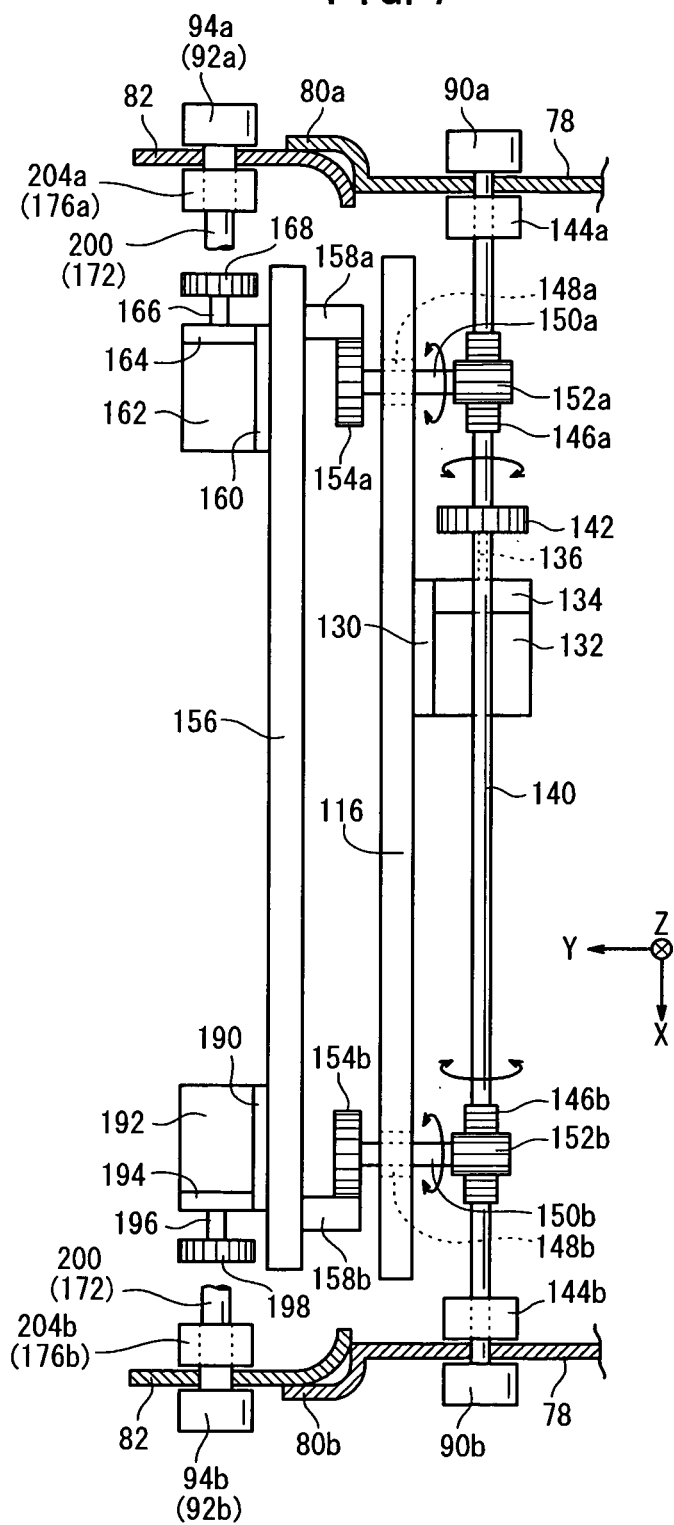
FIG. 7 is a plan view illustrating internal structural details of the biopsy needle moving mechanism shown in FIG. 3.
Figure 8:
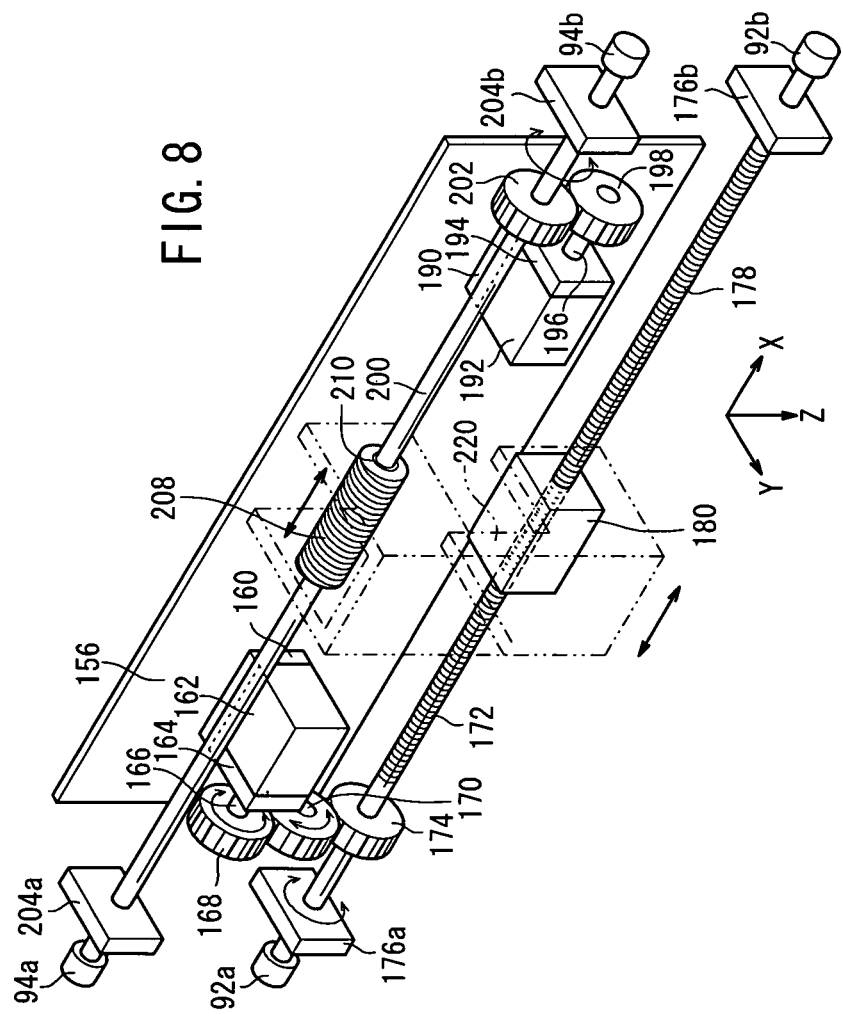
FIG. 8 is a perspective view illustrating internal structural details of the biopsy needle moving mechanism shown in FIG. 3.

As shown in FIGS. 7 and 8, the plate 156 is coupled operatively to rods 172, 200, which extend through side walls of the moving unit 82 (see FIGS. 2 and 3) along directions indicated by the arrow X, by rotational shafts 166, 196 of motors 162, 192 that are mounted on the plate 156 and by gears 168, 170, 174, 198, 202. The plate 156 also is connected to the moving unit 82 by a mount (not shown). As described above, the moving unit 86, which is mounted on the moving unit 82, serves to move the rods 58a, 58b, the biopsy needle holder 60, the biopsy needle support 62, and the biopsy needle 64 together in directions indicated by the arrow X.

When the plate 156 is moved along the direction indicated by the arrow Z, the moving unit 82, the moving unit 86, the rods 58a, 58b, the biopsy needle holder 60, the biopsy needle support 62, and the biopsy needle 64 also are moved together in unison along the direction indicated by the arrow Z.

Figure 6:
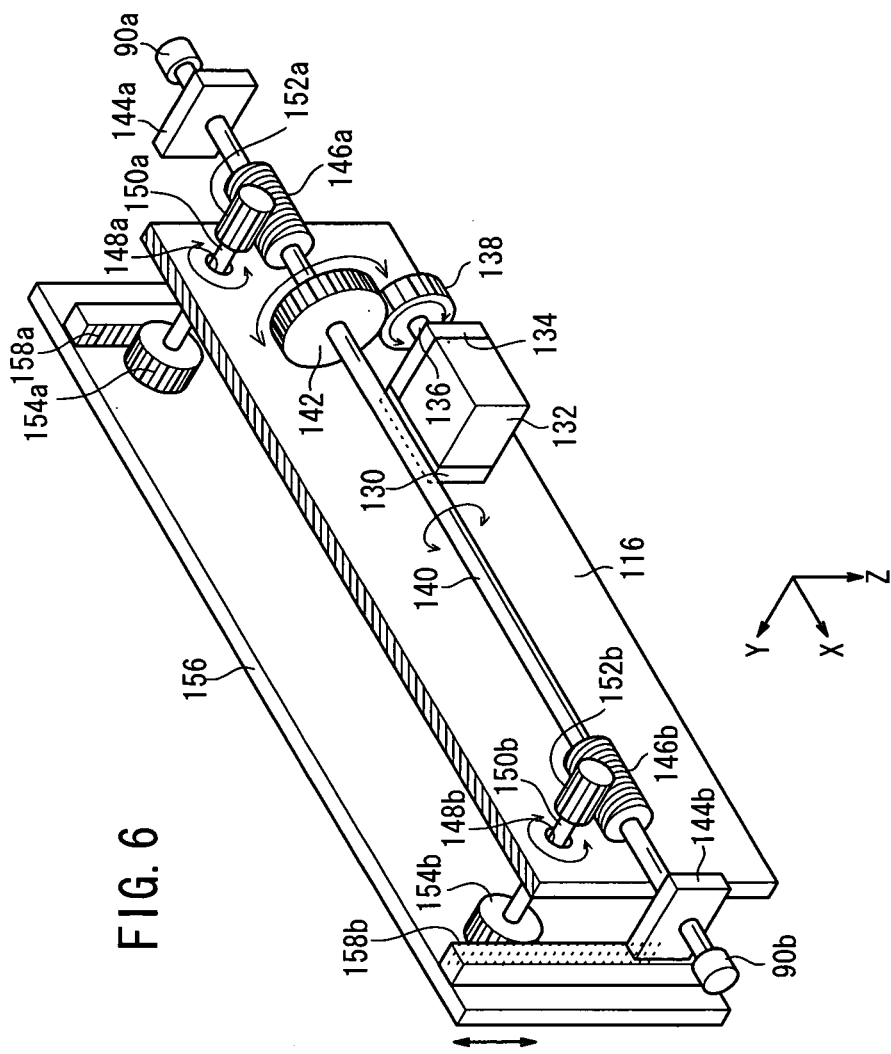
FIG. 6 is a perspective view illustrating internal structural details of the biopsy needle moving mechanism shown in FIG. 3.

Since the components shown in FIG. 6 through 8 are included in or are mounted on the moving unit 82, consequently, the components from the moving unit 82 to the biopsy needle 64 are moved (displaced) in unison with each other along directions indicated by the arrow Z when the moving unit 82 is moved along directions indicated by the arrow Z.

Since the handles 90a, 90b are mounted on both ends of the rod 140, it is possible for a doctor or radiological technician to turn the handles 90a, 90b in order to rotate the rod 140 about its axis, thereby displacing the plate 156 and the moving unit 82 along directions indicated by the arrow Z.

The rotary encoder 134 detects an angular displacement of the rotational shaft 136, and outputs the detected angular displacement to an external circuit. Since the plate 156 and the moving unit 82 move along directions indicated by the arrow Z upon rotation of the rotational shaft 136, the angular displacement of the rotational shaft 136 may be regarded as an angular displacement that depends on the displacement of the plate 156 and the moving unit 82 along directions indicated by the arrow Z.

Figure 9:
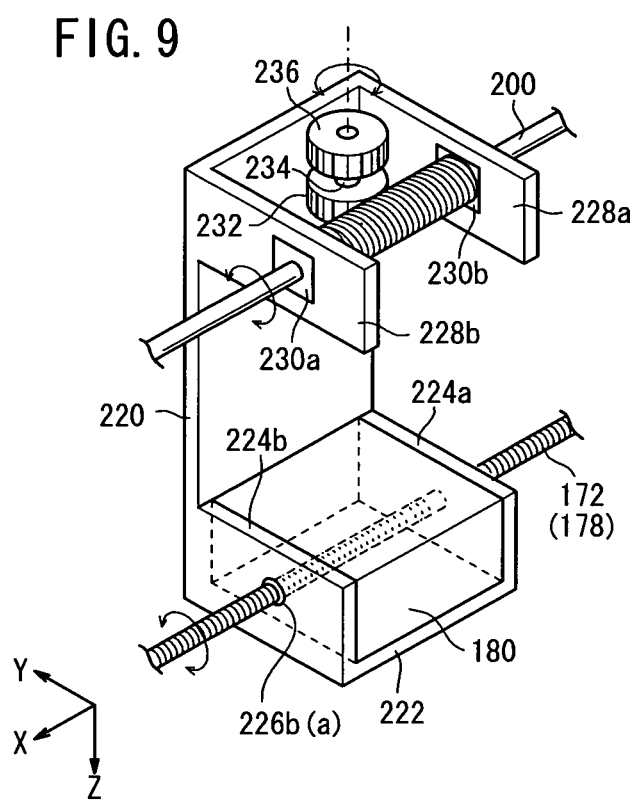
FIG. 9 is an enlarged perspective view of a portion of the internal structural details shown in FIG. 8.
Figure 10:
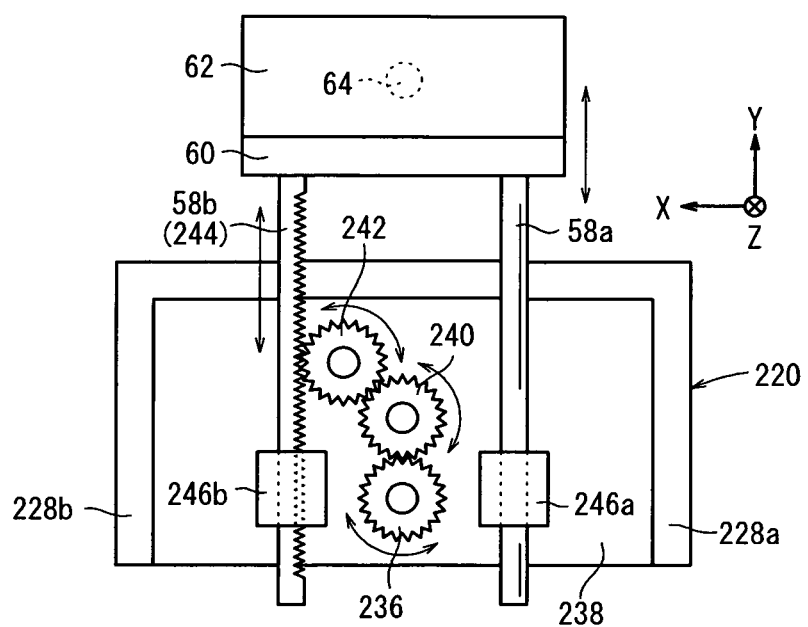
FIG. 10 is a plan view illustrating internal structural details of the biopsy needle moving mechanism shown in FIG. 3.

Among the internal structural details of the biopsy needle moving mechanism 56, structural details of a structure for producing movement in directions indicated by the arrow X will be described below with reference to FIGS. 7 through 9.

As shown in FIG. 8, the motor 162 and an encoder 164 are mounted by a mount plate 160 on a left side of the plate 156. The gear 168, which is mounted on the rotational shaft 166 of the motor 162, is held in mesh with the gear 170, which in turn is held in mesh with the gear 174 that is mounted on the rod 172. The rod 172 has opposite ends thereof coupled to the handles 92a, 92b.

More specifically, the rod 172 is supported rotatably by and extends through bearings 176a, 176b that are disposed inwardly of the side walls of the moving unit 82. The rod 172 also extends through the side walls of the moving unit 82 and opposite ends thereof are connected respectively to the handles 92a, 92b. The rod 172 has an externally threaded portion 178 that extends axially between the gear 174 and the bearing 176b. A slider 180 is threaded over the externally threaded portion 178 for movement along the rod 172.

When the motor 162 is energized to rotate the rotational shaft 166 about its axis, the rod 172 also is rotated about its axis by the gears 168, 170, 174. The slider 180, which is threaded over the externally threaded portion 178, converts rotation of the rod 172 into linear movement in directions indicated by the arrow X, and the slider 180 moves along the rod 172 in directions indicated by the arrow X.

The slider 180 is attached to a lower end of a U-shaped coupling member 220. The rods 58a, 58b are supported on an upper end of the coupling member 220 through a plate 238 and support members 246a, 246b (see FIG. 10). The rods 58a, 58b extend outwardly from the moving unit 86 through the groove 84. When the slider 180 is moved in directions indicated by the arrow X, the rods 58a, 58b, the biopsy needle holder 60, the biopsy needle support 62, and the biopsy needle 64 also are moved together in unison along directions indicated by the arrow X.

Since the components shown in FIG. 7 through 10 are included in or are mounted on the moving unit 82, consequently, the components disposed between the coupling member 220 and the biopsy needle 64 are moved (displaced) together in unison along directions indicated by the arrow X when the slider 180 is moved along directions indicated by the arrow X.

Since the handles 92a, 92b are mounted on both ends of the rod 172, it is possible for a doctor or radiological technician to turn the handles 92a, 92b in order to rotate the rod 172 about its axis, thereby displacing the slider 180 along directions indicated by the arrow X.

The rotary encoder 164 detects angular displacement of the rotational shaft 166, and outputs the detected angular displacement to an external circuit. Since the slider 180 moves along directions indicated by the arrow X upon rotation of the rotational shaft 166, the angular displacement of the rotational shaft 166 may be regarded as an angular displacement that depends on the displacement of the slider 180 along directions indicated by the arrow X.

Among the internal structural details of the biopsy needle moving mechanism 56, structural details of a structure for producing movement in directions indicated by the arrow Y will be described below with reference to FIGS. 7 through 10.

As shown in FIG. 8, the motor 192 and an encoder 194 are mounted on a right-hand side of the plate 156 by a mount plate 190. The gear 198, which is mounted on the rotational shaft 196 of the motor 192, is held in mesh with the gear 202, which is mounted on the rod 200. The rod 200 has opposite ends thereof coupled to the handles 94a, 94b.

More specifically, the rod 200 is supported rotatably and extends through bearings 204a, 204b that are disposed inwardly of the side walls of the moving unit 82. The rod 200 also extends through side walls of the moving unit 82. Opposite ends of the rod 200 are connected respectively to the handles 94a, 94b. A worm 208 is mounted centrally on the rod 200 with a sleeve-like spacer 210 interposed therebetween.

As described above, the slider 180 is attached to the lower end of the coupling member 220, which extends in directions indicated by the arrow Z. More specifically, the coupling member 220 includes a plate 222, which is positioned on a lower end thereof below the rod 172. Sides of the slider 180 are held in contact with side plates 224a, 224b that extend upwardly from opposite side edges of the plate 222. The side plates 224a, 224b have respective holes 226a, 226b defined therein through which the rod 172 extends.

The coupling member 220 also includes side plates 228a, 228b that extend from an upper end thereof along directions indicated by the arrow Y, and which are spaced upwardly from the side plates 224a, 224b in confronting relation thereto. The side plates 228a, 228b support respective bearings 230a, 230b through which the rod 200 extends. Thus, the rod 200 is supported rotatably by the bearings 230a, 230b. The worm 208 of the rod 200 is disposed between the bearings 230a, 230b.

When the coupling member 220 is displaced by the slider 180 in the direction indicated by the arrow X as the slider 180 is displaced in the same direction, the spacer 210 slides along the rod 200 under a force from the coupling member 220. When the rod 200 is rotated about its axis, the spacer 210 transmits rotation of the rod 200 to the worm 208.

More specifically, when the rod 200 is rotated about its axis, the spacer 210 transmits rotation of the rod 200 to the worm 208 in order to rotate the worm 208. When the slider 180 and the coupling member 220 are displaced in the direction indicated by the arrow X, the spacer 210 is displaced in unison with the worm 208 in the direction indicated by the arrow X.

The worm 208 is held in mesh with a worm wheel 232, which is mounted on a lower end of a vertical rod 234 and which extends along directions indicated by the arrow Z. The vertical rod 234 extends through a plate 238, which extends between upper ends of the side plates 228a, 228b, and has an upper end that is disposed above the plate 238 and supporting a gear 236. The gear 236 is held through a train of gears 240, 242 in mesh with a rack 244 provided on the rod 58b. The rods 58a, 58b extend through respective support members 246a, 246b, which are mounted on the plate 238. The rods 58a, 58b also extend through the groove 84 (see FIG. 3) in the direction indicated by the arrow Y.

When the motor 192 is energized to rotate the rotational shaft 196 about its axis, the rod 200 is rotated about its axis by the gears 198, 202. Rotation of the rod 200 about its axis (i.e., rotation about the direction indicated by the arrow X) is transmitted through the spacer 210 to the worm 208. The worm wheel 232 converts rotation of the worm 208 about its axis into rotation about the direction indicated by the arrow Z, thereby rotating the rod 234. Rotation of the rod 234 is transmitted through the gears 236, 240, 242 to the rack 244, which converts rotation of the rod 234 into linear movement along directions indicated by the arrow Y, thereby displacing the rod 58b longitudinally. As a result, the rods 58a, 58b, the biopsy needle holder 60, the biopsy needle support 62, and the biopsy needle 64 are moved together in unison along directions indicated by the arrow Y.

Since the components shown in FIG. 7 through 10 are included in or mounted on the moving units 82, 86, consequently, the components from the rods 58a, 58b to the biopsy needle 64 are moved (displaced) together in unison along directions indicated by the arrow Y when the rod 200 is rotated about its axis.

Since the handles 94a, 94b are mounted on both ends of the rod 200, it is possible for a doctor or radiological technician to turn the handles 94a, 94b and rotate the rod 200 about its axis, thereby displacing the rack 244 along directions indicated by the arrow Y.

The rotary encoder 194 detects an angular displacement of the rotational shaft 196, and outputs the detected angular displacement to an external circuit. Since the rack 244 moves along directions indicated by the arrow Y upon rotation of the rotational shaft 196, the angular displacement of the rotational shaft 196 may be regarded as an angular displacement that depends on the displacement of the rack 244 along directions indicated by the arrow Y.

Structural details of the biopsy needle moving mechanism 56 have been described above.

Hereinbelow, unless specified otherwise, it shall be assumed that the biopsy needle moving mechanism 56 moves the biopsy needle 64, etc., along directions indicated by the arrows X, Y and Z, and turns the biopsy needle 64 along directions indicated by the arrow 8, basically as shown in FIGS. 3 through 10.

A process of capturing images of the breast 22 with the mammographic apparatus 12 (see FIGS. 11 and 12), as well as a process of piercing the breast 22 with the biopsy needle 64 by actuating the biopsy needle moving mechanism 56 after such images have been captured (see FIGS. 13A through 16C), will be described below.

The mammographic apparatus 12 performs either one of a scout image capturing process (see FIG. 11) for irradiating the breast 22 with radiation 24a from the radiation source 26, which is disposed on the vertical axis (central axis 250a) of the solid-state detector 30, and a stereographic capturing process (see FIG. 12) for irradiating the breast 22 with radiation 24b, 24c from the radiation source 26, which is disposed on central axes 250b, 250c that are oblique to the central axis 250a. The solid-state detector 30 detects radiation 24a, 24b, 24c that has passed through the breast 22 in the scout or the stereographic capturing processes, and converts the detected radiation 24a, 24b, 24c into a radiographic image.

Figure 11:
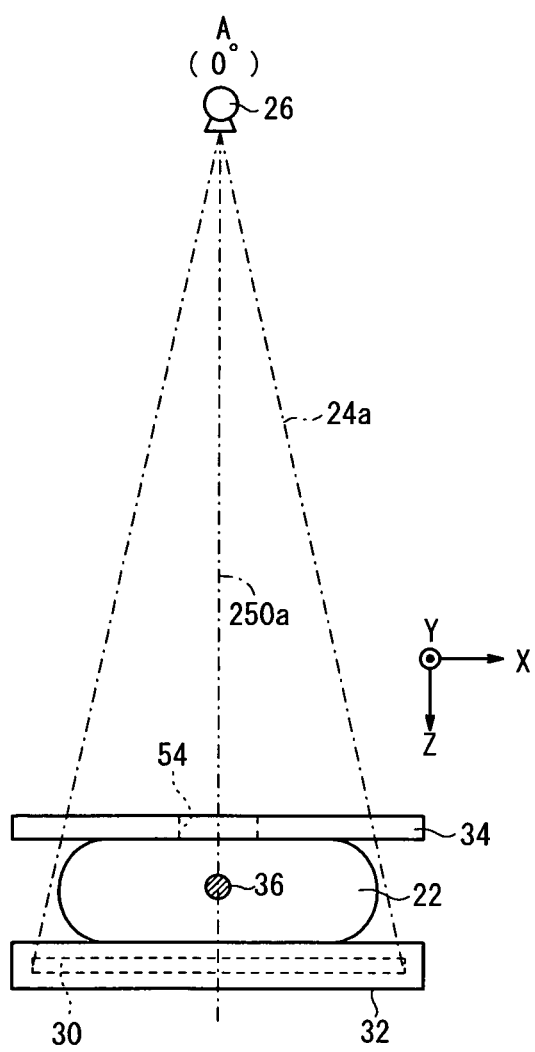
FIG. 11 is a schematic front elevational view showing by way of example a scout image capturing process.
Figure 12:
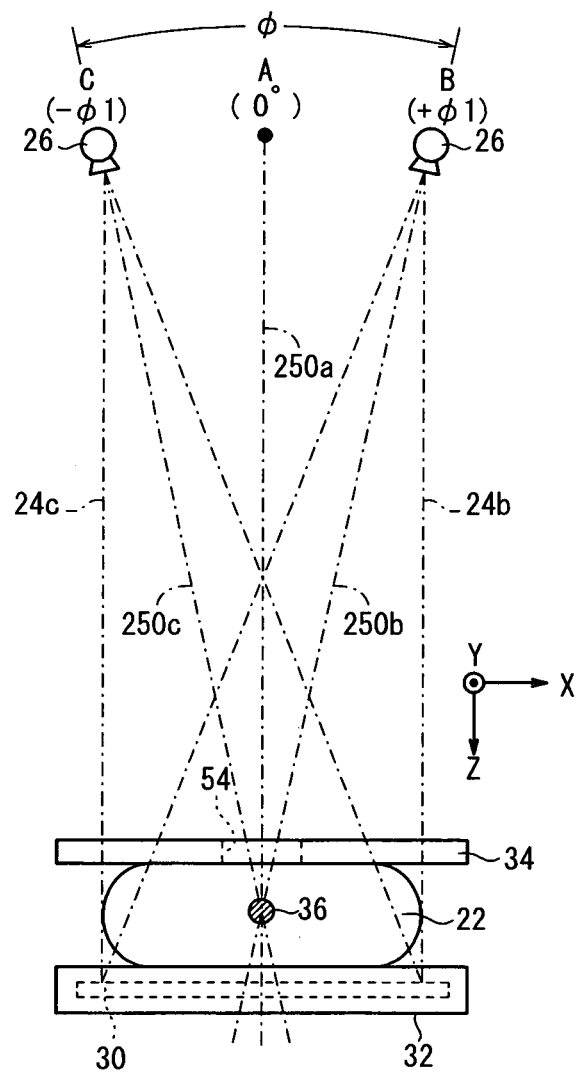
FIG. 12 is a schematic front elevational view showing by way of example a stereographic image capturing process.

In FIGS. 11 and 12, radiation 24a, 24b, 24c is shown as being applied to the breast 22, based on the assumption that the central axes 250a, 250b, 250c pass through the biopsy region 36, for example.

In the scout image capturing process shown in FIG. 11, the radiation source 26 is located at an image capturing angle of $\phi=0°$ with respect to the solid-state detector 30. The position of the radiation source 26 at the image capturing angle of $\phi=0°$ in the scout image capturing process is referred to as "position A". In the stereographic image capturing process shown in FIG. 12, the radiation source 26 is located at two different image capturing angles of $+\phi 1$, $-\phi 1$ with respect to the solid-state detector 30. Positions of the radiation source 26 at the respective image capturing angles of $+\phi 1$, $-\phi 1$ in the stereographic image capturing process are referred to as "position B" and "position C", respectively. The radiation source 26 is moved between positions A, B and C when the radiation source housing unit 28 is turned about the hinge 42 (see FIG. 1).

After the scout and stereographic capturing processes have been performed, the breast 22 is pierced with the biopsy needle 64 by actuating the biopsy needle moving mechanism 56.

Figure 13A:
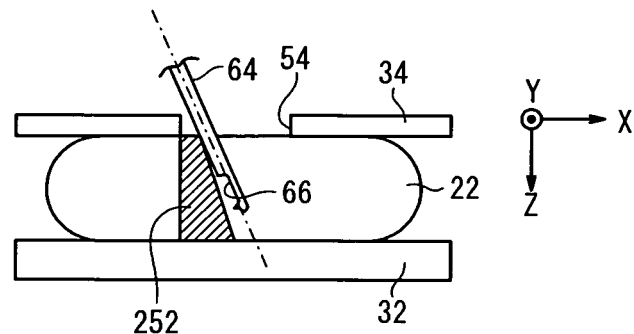
FIGS. 13A and 13B are views that illustrate problems with a conventional oblique piercing process.
Figure 13B:
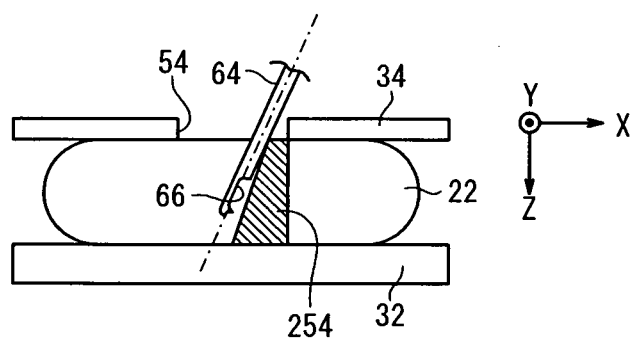
Figure 13C:
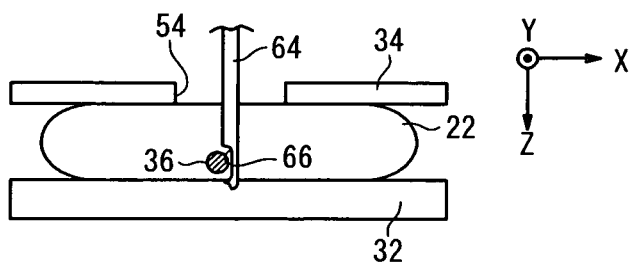
FIG. 13C is a view that illustrates problems with a conventional vertical piercing process.

FIGS. 13A through 13C are views illustrative of problems with conventional oblique and vertical piercing processes. Those parts shown in FIGS. 13A through 13C, which are identical to those shown in FIGS. 1 through 12, are denoted by identical reference characters.

Different processes for inserting the biopsy needle 64 into the breast 22 include a process for inserting the biopsy needle 64 into the breast 22 while the biopsy needle 64 is oriented obliquely to the direction in which the compression plate 34 compresses the breast 22, i.e., the direction indicated by the arrow Z, (i.e., an oblique piercing process, as shown in FIGS. 13A and 13B), and a process for inserting the biopsy needle 64 into the breast 22 along the direction in which the compression plate 34 compresses the breast 22 (i.e., a vertical piercing process shown, as shown in FIG. 13C). Commercially available biopsy apparatus, which are now in the market, sample tissue from the biopsy region 36 using either one of the oblique or the vertical piercing processes.

When the biopsy apparatus operates according to the oblique piercing process, since the biopsy needle 64 is inserted obliquely into the breast 22, the breast includes dead zones 252, 254 (shown by hatching in FIGS. 13A and 13B) therein from which tissue cannot be sampled, below an outer circumferential area of the opening 54 in the compression plate 34, regardless of the thickness of the breast 22. In order to sample tissue from such dead zones 252, 254, it is necessary to release the breast 22 from the compression plate 34, reposition the breast 22 so that the dead zones 252, 254 are placed at the center of the opening 54 as viewed in plan, compress the breast 22 again with the compression plate 34, and reinsert the biopsy needle 64 obliquely into the breast 22. Therefore, the oblique piercing process needs to be repeated in a sequence of successive steps of positioning the breast 22, compressing the breast 22, capturing an image of the breast 22, inserting the biopsy needle 64 into the breast 22, sampling tissue from the breast 22, and releasing the breast 22, as many times as the number of tissues to be sampled from the dead zones 252, 254. As a result, the examinee 20 is subjected to the examination procedure for a long period of time, and is exposed to an increased dose of radiation 24.

The biopsy apparatus, which operates according to the oblique piercing process, is capable of sampling tissue from a region in a relatively thin breast 22, which is close to the image capturing base 32, because the biopsy needle 64 is inserted obliquely into the breast 22.

The biopsy apparatus, which operates according to the vertical piercing process, is capable of sampling tissue from a biopsy region 36 in a breast 22, which is relatively thick. However, when the sampler 66 of the biopsy needle 64 is aligned with the biopsy region 36 in a breast 22 that is relatively thin and the biopsy needle 64 is inserted into the biopsy region 36, the tip end of the biopsy needle 64 tends to pierce through the relatively thin breast 22 (see FIG. 13C). According to the vertical piercing process, therefore, it is difficult to sample tissue from a region of a relatively thin breast 22, which is close to the image capturing base 32. In addition, the vertical piercing process fails to quickly sample breast tissue that is spread out in a planar direction along the compression plate 34 or the image capturing base 32.

Figure 14:
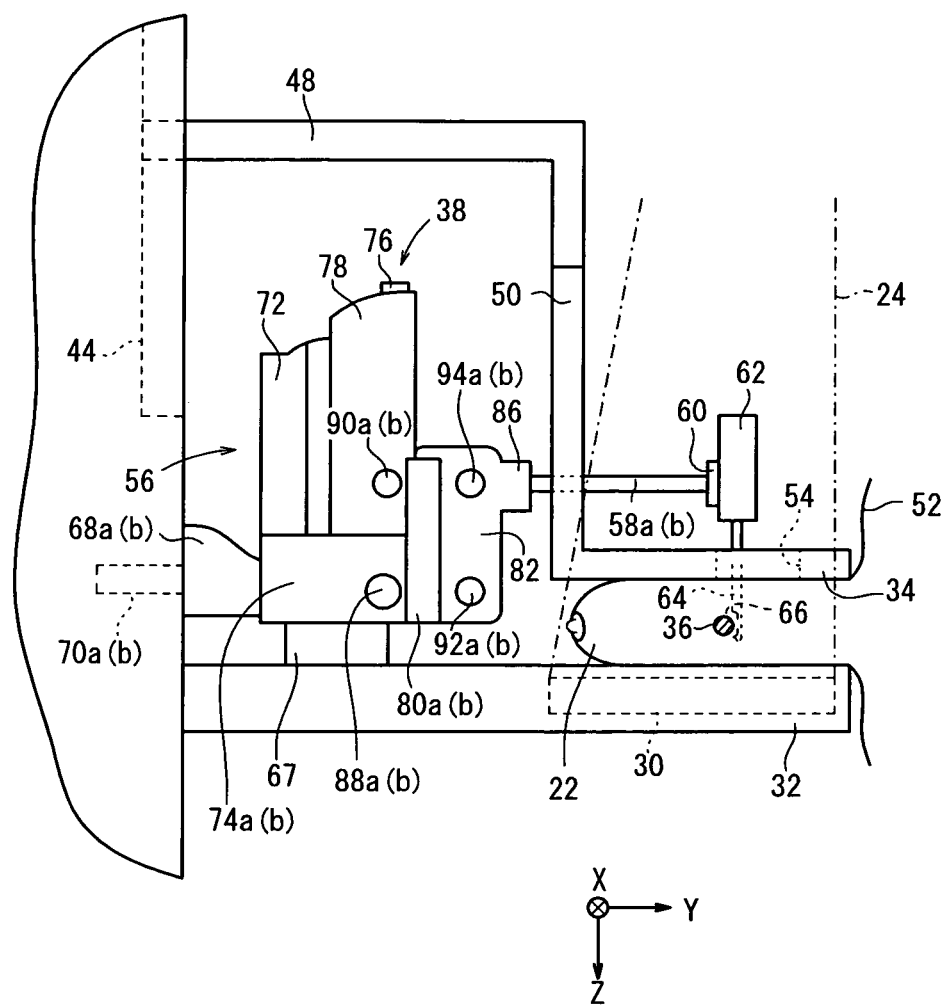
FIG. 14 is a side elevational view showing a vertical piercing process carried out by the biopsy needle moving mechanism shown in FIGS. 1 through 3.
Figure 16A:
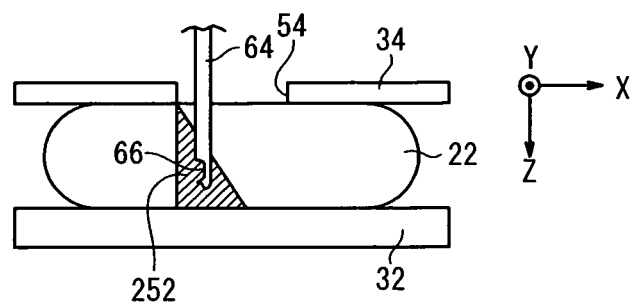
FIGS. 16A and 16B are views that illustrate the vertical piercing process shown in FIG. 14.
Figure 16B:
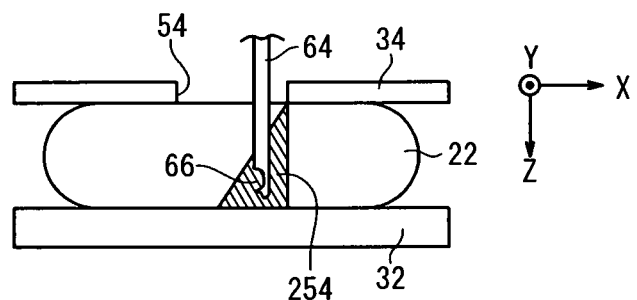

According to the present embodiment, as shown in FIG. 14, the biopsy needle moving mechanism 56 of the biopsy apparatus 10 performs a vertical piercing process on a breast 22 that is relatively thick, so as to move the biopsy needle 64 along three axes, i.e., along directions indicated by the arrows X, Y, Z, before the biopsy needle 64 samples tissue from the biopsy region 36. Consequently, as shown in FIGS. 16A and 16B, the sampler 66 of the biopsy needle 64 can be moved to the dead zones 252, 254 in a relatively thick breast 22.

Figure 15:
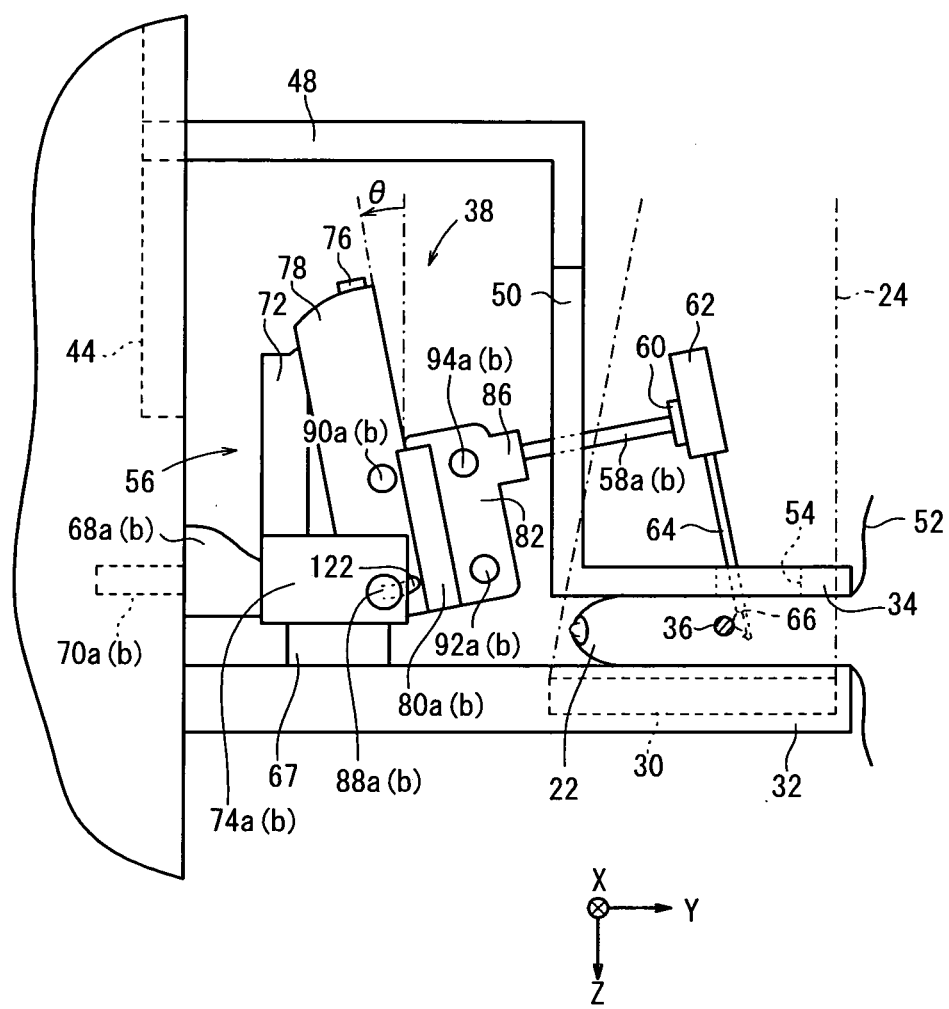
FIG. 15 is a side elevational view showing an oblique piercing process carried out by the biopsy needle moving mechanism shown in FIGS. 1 through 3.
Figure 16C:
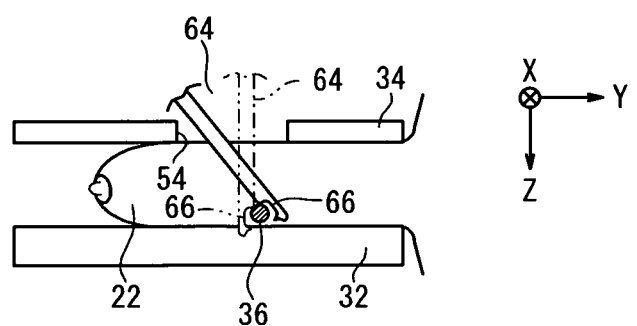
FIG. 16C is a view that illustrates the oblique piercing process shown in FIG. 15.

Furthermore, as shown in FIG. 15, the biopsy needle moving mechanism 56 of the biopsy apparatus 10 performs an oblique piercing process on a breast 22, which is relatively thin, so as to turn the biopsy needle 64 in the direction indicated by the arrow θ before the biopsy needle 64 samples tissue from the biopsy region 36. Consequently, as shown in FIG. 16C, the sampler 66 of the biopsy needle 64 can sample tissue from a breast 22 that is relatively thin without causing the biopsy needle 64 to pierce through the breast 22.

When performed, the oblique piercing process may be combined together with the vertical piercing process in order to move the biopsy needle 64 along three axes while also turning the biopsy needle 64 in directions indicated by the arrow θ.

Figure 17:
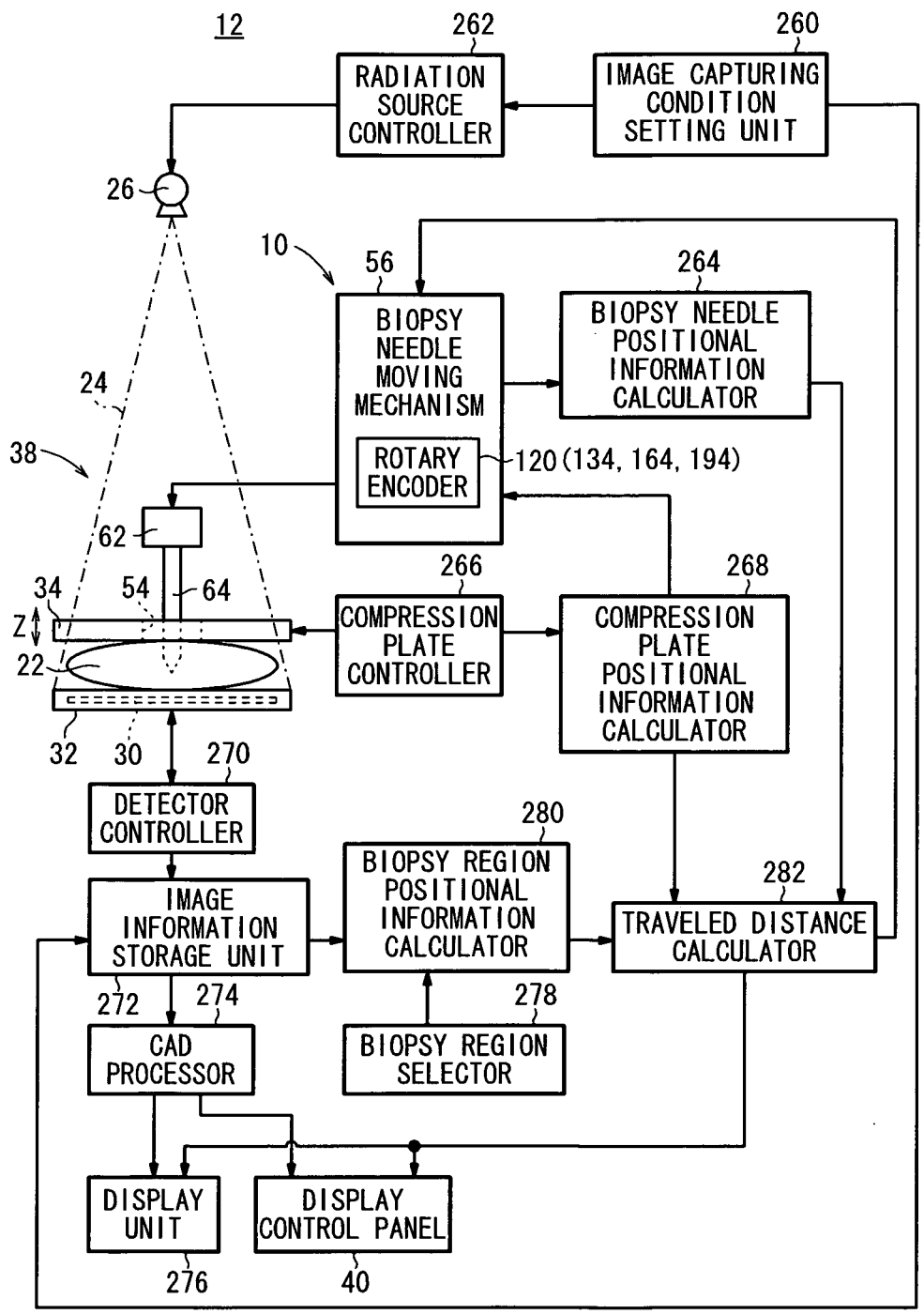
FIG. 17 is a block diagram of a mammographic apparatus incorporating the biopsy apparatus therein according to an embodiment of the present invention.

FIG. 17 shows in block form a mammographic apparatus 12 incorporating the biopsy apparatus 10 therein according to an embodiment of the present invention.

As shown in FIG. 17, the mammographic apparatus 12 includes an image capturing condition setting unit 260, a radiation source controller 262, a biopsy needle positional information calculator 264, a compression plate controller 266, a compression plate positional information calculator 268, a detector controller 270, an image information storage unit 272, a CAD (Computer Aided Diagnosis) processor 274, a display unit 276, a biopsy region selector 278, a biopsy region positional information calculator 280, and a traveled distance calculator 282.

The biopsy apparatus 10 is jointly made up from the biopsy hand assembly 38, the opening 54, the biopsy needle positional information calculator 264, the biopsy region selector 278, the biopsy region positional information calculator 280, and the traveled distance calculator 282. The biopsy apparatus 10, which is incorporated in the mammographic apparatus 12, is capable of sampling tissue from the biopsy region 36.

The image capturing condition setting unit 260 sets image capturing conditions including a tube current and a tube voltage of the radiation source 26, an irradiation dosage and an irradiation time of the radiation 24, an image capturing method such as a scout image capturing process or a stereographic image capturing process (see FIGS. 11 and 12), and an imaging sequence. The radiation source controller 262 controls the radiation source 26 according to the image capturing conditions.

When the biopsy needle moving mechanism 56 moves and/or turns the biopsy needle 64 to a given position, the rotary encoders 120, 134, 164, 194 detect and output respective angular displacements to the biopsy needle positional information calculator 264.

The compression plate controller 266 moves the compression plate 34 in directions indicated by the arrow Z. The detector controller 270 controls the solid-state detector 30 in order to store a radiographic image converted from the radiation 24 in the image information storage unit 272. When the scout image capturing process shown in FIG. 11 is carried out, a single radiographic image, which is captured at a single image capturing angle, is stored in the image information storage unit 272. When the stereographic image capturing process shown in FIG. 12 is carried out, two radiographic images, which are captured respectively at two image capturing angles (radiographic angles), are stored in the image information storage unit 272. When radiographic images are stored in the image information storage unit 272, the image capturing conditions set by the image information storage unit 272 also may be stored in the image information storage unit 272 together with the radiographic images.

The CAD processor 274 processes a radiographic image, which is stored in the image information storage unit 272, and displays the processed radiographic image on the display unit 276 and the display control panel 40.

The biopsy region selector 278 comprises a pointing device such as a mouse or the like. A doctor or radiological technician in charge who views the displayed contents, e.g., two radiographic images produced by the stereographic image capturing process, on the display unit 276 and/or the display control panel 40, can select from among a plurality of biopsy regions 36 displayed in the two radiographic images one from which tissue is to be removed, using the pointing device as the biopsy region selector 278. More specifically, the doctor or radiological technician selects a biopsy region 36 in one of the two radiographic images and also selects a corresponding biopsy region 36 in the other of the two radiographic images.

The biopsy region positional information calculator 280 calculates the three-dimensional position of the selected biopsy region 36 based on the positions of the selected biopsy regions 36 in the two radiographic images. The three-dimensional position of the selected biopsy region 36 can be calculated according to a known three-dimensional position calculating scheme utilized in the stereographic image capturing process.

When tissue is sampled from the biopsy region 36, the biopsy needle positional information calculator 264 calculates the three-dimensional position of the tip end of the biopsy needle 64 before the biopsy needle 64 samples tissue from the biopsy region 36, based on angular displacements supplied from the rotary encoders 120, 134, 164, 194.

If the biopsy needle moving mechanism 56 is not turned as a whole along directions indicated by the arrow θ, but the biopsy needle 64 is moved only along three axes, then the biopsy needle positional information calculator 264 calculates the three-dimensional position of the tip end of the biopsy needle 64 based on angular displacements from the rotary encoders 134, 164, 194 that depend on displacements along the three axes.

If the biopsy needle moving mechanism 56 is turned as a whole along directions indicated by the arrow θ, and the rotary encoder 120 outputs a detected angular displacement to the biopsy needle positional information calculator 264, then the biopsy needle positional information calculator 264 first calculates the three-dimensional position of the tip end of the biopsy needle 64 at a time when there is no turning movement along directions indicated by the arrow θ, and thereafter calculates the three-dimensional position of the tip end of the biopsy needle 64 at a time when the biopsy needle 64 is turned along directions indicated by the arrow θ.

Figure 5:
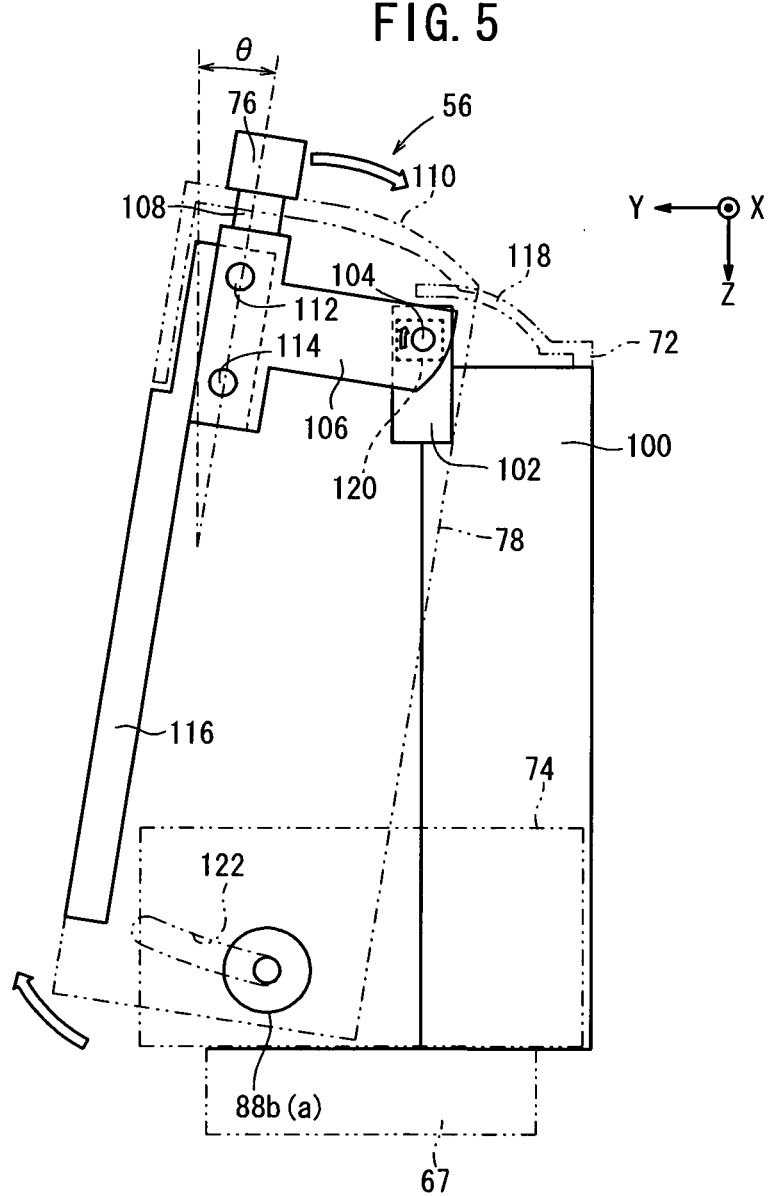
FIG. 5 is a side elevational view illustrating internal structural details of the biopsy needle moving mechanism shown in FIG. 3.

More specifically, it is assumed that the three-dimensional position of the tip end of the biopsy needle 64 before the biopsy needle 64 is turned, i.e., when the turning angle θ shown in FIGS. 4 and 14 along the X-Z plane is θ=0°, is represented by (X1, Y1, Z1), and the three-dimensional position of the tip end of the biopsy needle 64 after the biopsy needle 64 is turned, i.e., when the biopsy needle 64 is turned through the turning angle θ shown in FIGS. 5 and 15, is represented by (X2, Y2, Z2). Accordingly, since the biopsy needle 64 is turned along the Y-Z plane in directions indicated by the arrow θ, and is not turned in directions indicated by the arrow X, the relationship X1=X2 is satisfied. Therefore, using X1, Z1, and the turning angle θ, Y2 and Z2 are expressed by the following equations (1) and (2):

$$Y2 = Y1 \times \cos\theta - Z1 \times \sin\theta \qquad (1)$$

$$Z2 = Y1 \times \sin\theta + Z1 \times \cos\theta \qquad (2)$$

Using equations (1) and (2) based on the known two-dimensional coordinate transformation (coordinate transformation in the Y-Z plane along which the biopsy needle 64 is turned), the biopsy needle positional information calculator 264 calculates the three-dimensional position (X2, Y2, Z2) of the tip end of the biopsy needle 64 after the biopsy needle 64 is turned, from the three-dimensional position (X1, Y1, Z1) of the tip end of the biopsy needle 64 before the biopsy needle 64 is turned.

The compression plate positional information calculator 268 calculates the positional information of the compression plate 34, which has been moved with respect to the image capturing base 32 by the compression plate controller 266. Since the compression plate 34 presses the breast 22 with respect to the image capturing base 32 and holds the breast 22 in a pressed state, the positional information of the compression plate 34 represents thickness information of the breast 22 when the breast 22 is pressed.

The traveled distance calculator 282 determines which, from among the oblique piercing process and the vertical piercing process, is to be used to insert the biopsy needle 64 into the breast 22, and calculates the distance by which the biopsy needle 64 is to move with respect to the biopsy region 36 according to the selected piercing process, based on the three-dimensional position of the biopsy region 36, which has been calculated by the biopsy region positional information calculator 280, the three-dimensional position of the tip end of the biopsy needle 64, which has been calculated by the biopsy needle positional information calculator 264, and the position of the compression plate 34, which has been calculated by the compression plate positional information calculator 268 (representing the thickness of the breast 22).

More specifically, if the biopsy needle 64 is not turned in directions indicated by the arrow θ (see FIGS. 4 and 14), then the traveled distance calculator 282 calculates the difference (ΔX1, ΔY1, ΔZ1)=(Xt−X1, Yt−Y1, Zt−Z1) between the three-dimensional position (Xt, Yt, Zt) of the biopsy region 36, which has been calculated by the biopsy region positional information calculator 280, and the three-dimensional position (X1, Y1, Z1) of the tip end of the biopsy needle 64, which has been calculated by the biopsy needle positional information calculator 264, as the traveled distance (ΔX1, ΔY1, ΔZ1) of the biopsy needle 64.

If the biopsy needle 64 is turned in directions indicated by the arrow θ (see FIGS. 5 and 15), then the traveled distance calculator 282 calculates the difference (ΔX2, ΔY2, ΔZ2)=(Xt−X2, Yt−Y2, Zt−Z2) between the three-dimensional position (Xt, Yt, Zt) of the biopsy region 36, which has been calculated by the biopsy region positional information calculator 280, and the three-dimensional position (X2, Y2, Z2) of the tip end of the biopsy needle 64, which has been calculated by the biopsy needle positional information calculator 264, after the biopsy needle 64 has been turned.

Since X1=X2 and ΔX1=ΔX2, the difference (ΔX2, ΔY2, ΔZ2) represents the traveled distance of the biopsy needle 64 after the biopsy needle is turned with respect to the biopsy region 36, as viewed in the X-Y-Z coordinate system.

Then, the traveled distance calculator 282 determines a distance (ΔX', ΔY', ΔZ') that the biopsy needle 64 has traveled after the biopsy needle 64 is turned with respect to the biopsy region 36, as viewed in an X'-Y'-Z' coordinate system, which is rotated from the X-Y-Z coordinate system through the turning angle θ.

Since the biopsy needle 64 is turned in the Y-Z plane in directions indicated by the arrow θ, and the biopsy needle 64 is not turned in directions indicated by arrow X, as described above, the relationship ΔX1=ΔX2=ΔX' is satisfied. Using ΔY2, ΔZ2, and the turning angle θ, ΔY' and ΔZ' can be expressed by the following equations (3) and (4):

$$\Delta Y' = \Delta Y2 \times \cos\theta - \Delta Z2 \times \sin\theta \qquad (3)$$

$$\Delta Z' = \Delta Y2 \times \sin\theta + \Delta Z2 \times \cos\theta \qquad (4)$$

Therefore, using the equations (3) and (4), and based on the known two-dimensional coordinate transformation (i.e., a coordinate transformation in the Y-Z plane along which the biopsy needle 64 is turned), the traveled distance calculator 282 determines the traveled distance of the biopsy needle 64 after the biopsy needle 64 is turned.

The biopsy needle moving mechanism 56 therefore can move the biopsy needle 64 according to a piercing process (i.e., the oblique piercing process or the vertical piercing process), which is determined by the traveled distance calculator 282 and the traveled distance of the biopsy needle 64 as calculated by the traveled distance calculator 282, in order for the biopsy needle 64 to sample tissue from the biopsy region 36.

While the biopsy needle moving mechanism 56 moves and/or turns the biopsy needle 64, the rotary encoders 120, 134, 164, 194 are capable of detecting and outputting angular displacements to the biopsy needle positional information calculator 264. In this case, the biopsy needle positional information calculator 264 calculates the current three-dimensional position of the tip end of the biopsy needle 64 (actual three-dimensional position) based on the angular displacements output from the rotary encoders 120, 134, 164, 194. The traveled distance calculator 282 compares the traveled distance, which is indicated to the biopsy needle moving mechanism 56, and the actual traveled distance based on the current three-dimensional position of the tip end of the biopsy needle 64 (actual three-dimensional position), which has been calculated by the biopsy needle positional information calculator 264. If the difference between the compared travel distances falls outside of an allowable range, then the traveled distance calculator 282 displays a judgment, which indicates that the biopsy needle moving mechanism 56 has not moved the biopsy needle 64 in accordance with the indicated traveled distance, on the display unit 276 and the display control panel 40, thereby indicating such a judgment to a doctor or radiological technician.

The biopsy apparatus 10 and the mammographic apparatus 12 according to the present embodiment are constructed basically as described above. Operations of the biopsy apparatus 10 and the mammographic apparatus 12 will be described below with reference to the flowchart shown in FIG. 18.

Before radiographic images are captured, image capturing conditions, including a tube current and a tube voltage depending on the breast 22, an irradiation dosage and an irradiation time of the radiation 24, an image capturing method, and an imaging sequence are set in the image capturing condition setting unit 260 (see FIG. 17). A doctor or radiological technician assembles the biopsy hand assembly 38 onto the mammographic apparatus 12, and securely positions the biopsy hand assembly 38 over the image capturing base 32.

In step S1, a doctor or radiological technician positions the breast 22 of the examinee 20. More specifically, a doctor or radiological technician places the breast 22 in a predetermined position on the image capturing base 32, i.e., a position facing toward the opening 54, and operates the compression plate controller 266 in order to move the compression plate 34 toward the image capturing base 32 in the direction indicated by the arrow Z, thereby compressing and positioning the breast 22.

Thereafter, the breast 22 is compressed and secured between the image capturing base 32 and the compression plate 34. The compression plate positional information calculator 268 calculates positional information of the compression plate 34 with respect to the image capturing base 32, and outputs the calculated positional information to the traveled distance calculator 282 and the biopsy needle moving mechanism 56.

When the biopsy needle moving mechanism 56 (see FIGS. 3 through 10) is supplied with positional information of the compression plate 34 from the compression plate positional information calculator 268, the biopsy needle moving mechanism 56 judges that the breast 22 is compressed, and energizes the motors 132, 162, 192. Because the rods 58a, 58b are displaced by the energized motors 132, 162, 192 in the direction indicated by the arrow Y, the biopsy needle holder 60, without the biopsy needle support 62 installed thereon, moves through the opening defined between the compression plate connector 50 and the compression plate 34 and up to a given position located near the chest wall 52, i.e., at a position where the biopsy needle support 62 will not interfere with the radiation source housing unit 28 and the chest wall 52 when the biopsy needle support 62 is installed on the biopsy needle holder 60. After the biopsy needle holder 60 has reached such a position, a doctor or radiological technician installs the biopsy needle support 62, with the biopsy needle 64 mounted thereon, on the biopsy needle holder 60.

The rotary encoders 134, 164, 194 detect angular displacements of the rotational shafts 136, 166, 196 at a time when the biopsy needle holder 60 has been moved to the given position, and the rotary encoders 134, 164, 194 output the detected angular displacements to the biopsy needle positional information calculator 264. When the biopsy needle support 62 is installed on the biopsy needle holder 60, therefore, the biopsy needle positional information calculator 264 can calculate the three-dimensional position of the biopsy needle 64 based on the angular displacements supplied thereto.

After the above preparatory process is completed, in step S2, the mammographic apparatus 12 energizes the radiation source 26 in order to perform a scout image capturing process on the breast 22.

More specifically, the radiation source housing unit 28 is turned about the hinge 42 (see FIG. 1) so as to move the radiation source 26 to the position A (see FIG. 11). Thereafter, a doctor or radiological technician turns on an exposure switch, not shown. The radiation source controller 262 energizes the radiation source 26 placed in position A (0°), according to image capturing conditions for the scout image capturing process that are supplied from the image capturing condition setting unit 260.

Radiation 24a emitted from the radiation source 26 in position A is applied to the breast 22. Such radiation 24a then passes through the breast 22, and is detected by the solid-state detector 30 as radiation representing a single radiographic image of the breast 22. The detector controller 270 controls the solid-state detector 30 to acquire a single radiographic image from the detected radiation, and to store the acquired radiographic image in the image information storage unit 272. The CAD processor 274 processes the radiographic image stored in the image information storage unit 272, and displays the processed radiographic image on the display unit 276 and the display control panel 40. At this time, a doctor or radiological technician can confirm that the breast 22 including the biopsy region 36 is positioned within a radiographic image capturing range.

In step S3, the mammographic apparatus 12 energizes the radiation source 26 in order to perform a stereographic image capturing process on the breast 22.

The mammographic apparatus 12 turns the radiation source housing unit 28 about the hinge 42 (see FIG. 1) in order to place the radiation source 26 in position B (see FIG. 12), for example. Then, a doctor or radiological technician turns on the exposure switch. The radiation source controller 262 energizes the radiation source 26, which has been placed in position B (+φ1), according to the image capturing conditions for the stereographic image capturing process that are supplied from the image capturing condition setting unit 260.

Radiation 24b emitted from the radiation source 26 in position B is applied to the breast 22. Such radiation 24b then passes through the breast 22, and is detected by the solid-state detector 30 as radiation representing a single radiographic image of the breast 22. The detector controller 270 controls the solid-state detector 30 to acquire a single radiographic image from the detected radiation, and to store the acquired radiographic image, together with the image capturing conditions, in the image information storage unit 272.

After a single radiographic image has been captured based on radiation emitted from the radiation source 26 in position B, the mammographic apparatus 12 moves the radiation source 26 to position C shown in FIG. 12, and captures a second radiographic image of the breast 22 based on radiation 24c emitted from the radiation source 26 in position C.

The second radiographic image is acquired and stored, together with the image capturing conditions, in the image information storage unit 272. Thereafter, the CAD processor 274 processes the two radiographic images stored in the image information storage unit 272, and displays the processed radiographic images on the display unit 276 and the display control panel 40.

In step S4, a doctor or radiological technician views the two radiographic images displayed on the display unit 276 and/or the display control panel 40, and selects a biopsy region 36 from which tissue is to be sampled, from the biopsy regions 36 displayed in the two radiographic images, using the biopsy region selector 278. Then, the biopsy region positional information calculator 280 calculates the three-dimensional position of the selected biopsy region 36, and displays the calculated three-dimensional position on the display unit 276 and the display control panel 40.

In step S5, a doctor or radiological technician sterilizes and administers a local anesthesia to the breast 22 before the biopsy needle 64 pierces the breast 22.

In step S6, the mammographic apparatus 12 again performs a stereographic image capturing process on the breast 22, because the biopsy region 36 may have become positionally displaced by administration of the local anesthesia in step S5.

In step S7, a doctor or radiological technician makes an incision in the surface of the breast 22 with a surgical knife, at a position where the biopsy needle 64 is to be inserted. The biopsy needle 64 then is inserted through the incision into the breast 22.

The two radiographic images acquired by the stereographic image capturing process in step S6 are displayed on the display unit 276 and the display control panel 40. A doctor or radiological technician views the two displayed radiographic images, and again selects a biopsy region 36 from which tissue is to be sampled, from the biopsy regions 36 displayed in the two radiographic images, using the biopsy region selector 278. Then, the biopsy region positional information calculator 280 again calculates the three-dimensional position of the selected biopsy region 36.

Since the biopsy needle positional information calculator 264 has already calculated the present three-dimensional position of the biopsy needle 64 in step S1, the biopsy needle positional information calculator 264 outputs the calculated three-dimensional position to the traveled distance calculator 282.

The traveled distance calculator 282 calculates the distance by which the biopsy needle 64 is to move toward the incision, based on the three-dimensional position of the biopsy region 36, which has been calculated by the biopsy region positional information calculator 280, the three-dimensional position of the tip end of the biopsy needle 64, which has been calculated by the biopsy needle positional information calculator 264, and the position of the compression plate 34, which has been calculated by the compression plate positional information calculator 268, and outputs the calculated distance to the biopsy needle moving mechanism 56. The biopsy needle moving mechanism 56 then moves the tip end of the biopsy needle 64 toward the incision according to the calculated distance by which the biopsy needle 64 is to move.

In step S8, the mammographic apparatus 12 performs a stereographic image capturing process again, in the same manner as the stereographic image capturing process performed in step S6, in order to confirm whether or not the biopsy needle 64 has been inserted along a direction aligned with the biopsy region 36.

When the two radiographic images captured in the stereographic image capturing process in step S8 are displayed on the display unit 276 and the display control panel 40, a doctor or radiological technician operates the biopsy region selector 278 in order to select once again a biopsy region 36 from which tissue is to be sampled, from the biopsy regions 36 displayed in the two radiographic images, in the same manner as in steps S4 and S7. Then, the biopsy region positional information calculator 280 calculates the three-dimensional position of the selected biopsy region 36, and displays the calculated three-dimensional position on the display unit 276 and the display control panel 40, while also outputting the calculated three-dimensional position to the traveled distance calculator 282.

In step S9, the rotary encoders 120, 134, 164, 194 detect and output to the biopsy needle positional information calculator 264 respective angular displacements depending on movement of the biopsy needle 64 up to the incision. The biopsy needle positional information calculator 264 calculates the three-dimensional position of the tip end of the biopsy needle 64 based on the supplied angular displacements, and outputs the calculated three-dimensional position to the traveled distance calculator 282. The traveled distance calculator 282 determines a piercing process for the biopsy needle 64, and calculates the distance by which the biopsy needle 64 is to move with respect to the biopsy region 36, based on the three-dimensional position of the biopsy region 36, the three-dimensional position of the tip end of the biopsy needle 36, which has been calculated by the biopsy needle positional information calculator 264, and positional information of the compression plate 34, which has been calculated by the compression plate positional information calculator 268. The traveled distance calculator 282 outputs the determined piercing process and the calculated distance to the biopsy needle moving mechanism 56.

Thereafter, the biopsy needle moving mechanism 56 can move the sampler 66 of the biopsy needle 64 to the biopsy region 36 according to the piercing process (i.e., the oblique piercing process or the vertical piercing process) determined by the traveled distance calculator 282, and the traveled distance of the biopsy needle 64 as calculated by the traveled distance calculator 282.

In step S10, the mammographic apparatus 12 performs a stereographic image capturing process again, in the same manner as the stereographic image capturing process performed in steps S6 and S8, in order to confirm whether the position of the biopsy region 36 and the position and direction of the sampler 66 are in agreement with each other.

When the two radiographic images captured in the stereographic image capturing process in step S10 are displayed on the display unit 276 and the display control panel 40, a doctor or radiological technician can easily confirm from the displayed radiographic images whether or not the position of the biopsy region 36 and the position and direction of the sampler 66 are actually in agreement with each other.

In step S11, the biopsy needle 64 starts to sample tissue from the biopsy region 36 under suction. Thereafter, in step S12, the sampled tissue is inspected by an inspection apparatus (not shown) to check if the tissue is calcified or not.

In step S13, the mammographic apparatus 12 again performs a stereographic image capturing process, in the same manner as the stereographic image capturing process performed in steps S6, S8 and S10, in order to confirm that tissue has been sampled from the biopsy region 36.

When the two radiographic images captured in the stereographic image capturing process in step S13 are displayed on the display unit 276 and the display control panel 40, a doctor or radiological technician can easily confirm from the displayed radiographic images whether tissue has been properly sampled from the biopsy region 36.

Figure 18:
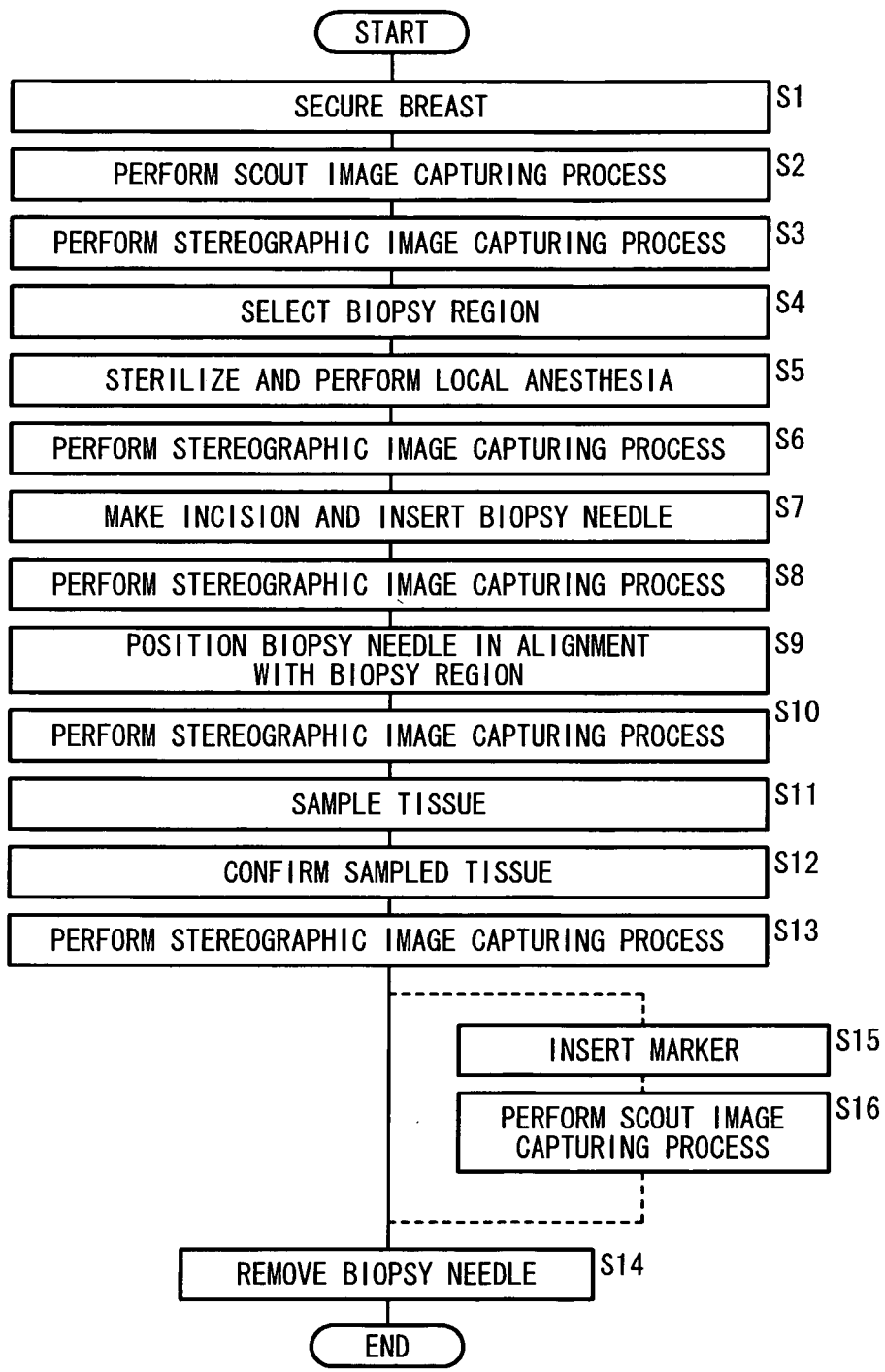
FIG. 18 is a flowchart of an operation sequence of the mammographic apparatus and the biopsy apparatus.

Thereafter, in step S14, the biopsy needle moving mechanism 56 moves the biopsy needle 64 in a direction opposite to the direction in step S9, so as to remove the biopsy needle 64 from the breast 22. The operation sequence shown in FIG. 18 is now brought to an end.

After all of the tissue has been sampled from the biopsy region 36, the position of the biopsy region 36 may not be able to be clearly spotted when such a position is subsequently confirmed. To prevent such a situation, prior to step S14, a marker is inserted into the biopsy region 36. More specifically, in step S15, a marker made of stainless steel is inserted into the biopsy region 36 by the sampler 66 of the biopsy needle 64. Thereafter, the mammographic apparatus 12 performs a scout image capturing process again, in the same manner as the scout image capturing process performed in step S2, in order to confirm the inserted marker in step S16. The display unit 276 and the display control panel 40 display a single radiographic image acquired by the scout image capturing process, whereby a doctor or radiological technician can easily confirm the marker that has been inserted into the biopsy region 36. After the marker has been confirmed, the biopsy needle 64 is removed from the breast 22 in step S14.

As described above, the biopsy apparatus 10 according to the present embodiment and the mammographic apparatus 12 incorporating the biopsy apparatus 10 therein move the biopsy needle 64 along three axes, i.e., along directions indicated by the arrows X, Y, Z, and/or turn the biopsy needle 64 along directions indicated by the arrow θ obliquely with respect to the breast 22, based on the distance that the biopsy needle 64 is moved with respect to the biopsy region 36. Accordingly, it is possible to sample tissue from the biopsy region 36 according to an appropriate piercing process that depends on the thickness of the breast 22.

More specifically, if the breast 22 is relatively thick, then tissue may be sampled from the biopsy region 36 according to a piercing process (vertical piercing process), which moves the biopsy needle 36 along three axes. If the breast 22 is relatively thin, then tissue may be sampled from the biopsy region 36 according to a piercing process (oblique piercing process), which turns the biopsy needle 64 obliquely with respect to the breast 22.

Since the biopsy needle 64 is moved and/or turned in a manner to take advantage of the vertical piercing process or the oblique piercing process in order to sample tissue from the biopsy region 36, tissue can be sampled reliably and efficiently from the biopsy region 36 regardless of the thickness of the breast 22. Since the vertical piercing process or the oblique piercing process is selected depending on characteristics of the breast 22, it is possible to prevent dead zones 252, 254 from occurring in the breast 22.

In light of the advantages of the vertical piercing process, since the biopsy needle 64 is inserted in the same direction as the direction in which the breast 22 is compressed, i.e., in the direction indicated by the arrow Z, when the sampler 66 of the biopsy needle 64 is moved into the biopsy region 36, i.e., when the breast 22 is pierced, in step S9, the sampler 66 and the biopsy region 36 are prevented from being brought out of positional alignment with each other, and the entire region within the opening 54 can be pierced by the biopsy needle 64. In addition, the depth by which the biopsy needle 64 is moved toward the biopsy region 36 can be minimized.

In light of the advantages of the oblique piercing process, the biopsy needle 64 can be inserted into the breast 22 in order to bring the sampler 66 into an optimum position with respect to the biopsy region 36. Also, the biopsy needle 64 can be inserted into the breast 22 so as to cause the sampler 66 to reach the biopsy region 36 reliably, even when the breast 22 is relatively thin.

According to the present embodiment, when the biopsy needle 64 is turned, the three-dimensional position of the tip end of the biopsy needle 64 is calculated based on the turning angle θ (angular displacement) of the biopsy needle 64. More specifically, according to equations (1) and (2), the biopsy needle positional information calculator 264 can easily calculate the three-dimensional position of the biopsy needle 64 after the biopsy needle 64 has been turned. Therefore, the biopsy needle positional information calculator 264 is not required to implement an algorithm for calculating the three-dimensional position of the biopsy needle 64 when the biopsy needle 64 is not turned, as well as an algorithm for calculating the three-dimensional position of the biopsy needle 64 when the biopsy needle 64 is turned. Rather, the biopsy needle positional information calculator 264 only is required to implement an algorithm for calculating the three-dimensional position of the biopsy needle 64 when the biopsy needle 64 is turned. Accordingly, the load imposed on and the storage capacity required by the biopsy needle positional information calculator 264 in calculating the three-dimensional position of the biopsy needle 64 can be reduced. As a result, the time required to calculate the three-dimensional position of the biopsy needle 64 is shortened, and the cost of the biopsy apparatus 10 can be lowered.

According to equations (3) and (4), the traveled distance calculator 282 can easily determine the distance that the tip end of the biopsy needle 64, after turning thereof, is to move toward the biopsy region 36.

According to the present embodiment, as described above, since tissue can reliably and efficiently be sampled from the biopsy region 36 regardless of the thickness of the breast 22, the time required to sample tissue from the biopsy region 36 is reduced, and the dosage of radiation 24 applied to the examinee 20 is lowered.

As shown in FIGS. 3 through 10, the biopsy needle moving mechanism 56 is capable of moving the biopsy needle 64, the biopsy needle support 62, and the biopsy needle holder 60 along respective directions indicated by the arrows X, Y, Z, and also is capable of turning the biopsy needle 64, the biopsy needle support 62, and the biopsy needle holder 60 along directions indicated by the arrow θ. The rotary encoders 120, 134, 164, 194 detect and output respective angular displacements of the shaft 104 and the rotational shafts 136, 166, 196 depending on the displacements and turning angle, which are output to the biopsy needle positional information calculator 264. The biopsy needle positional information calculator 264 calculates the three-dimensional position of the tip end of the biopsy needle 64 before the biopsy needle 64 is turned, based on angular displacements output from the rotary encoders 134, 164, 194, and also calculates the three-dimensional position of the tip end of the biopsy needle 64 after the biopsy needle is turned, based on the angular displacement output from the rotary encoder 120.

Therefore, the biopsy needle 64, the biopsy needle support 62, and the biopsy needle holder 60 can reliably and efficiently be turned and moved along three respective axes, and angular displacements, which are based on displacements along the three axes and the turning angle, can reliably be detected and output to the biopsy needle positional information calculator 264. Thus, the biopsy needle positional information calculator 264 can accurately calculate the three-dimensional position of the biopsy needle 64.

The biopsy needle moving mechanism 56 is turned substantially as a whole with respect to the base 67 to thereby turn the biopsy needle holder 60. Therefore, the biopsy needle holder 60 does not require a component, e.g., a motor, for turning the biopsy needle 64. Therefore, the biopsy needle holder 60 is reduced in size and weight, and hence, the mammographic apparatus 12 also is reduced in size and weight.

The traveled distance calculator 282 is capable of monitoring whether or not the biopsy needle moving mechanism 56 is moving and/or turning the biopsy needle holder 60 based on the traveled distance output to the biopsy needle moving mechanism 56. The traveled distance calculator 282 calculates the actual distance traveled by the biopsy needle holder 60. If the difference between the traveled distance output to the biopsy needle moving mechanism 56 and the actual distance traveled by the biopsy needle holder 60 falls outside of an allowable range, then the traveled distance calculator 282 displays a judgment on the display unit 276 and the display control panel 40, in order to indicate such a judgment to a doctor or radiological technician.

Since one can easily recognize whether the biopsy needle moving mechanism 56 is moving the biopsy needle 64 or not based on the traveled distance output from the traveled distance calculator 282, a doctor or radiological technician can quickly take actions, such as shutting down of biopsy apparatus 10, when such a judgment (warning) is indicated.

The biopsy needle moving mechanism 56 includes the rods 70a, 70b by which the biopsy needle moving mechanism 56 is detachably installed on the mammographic apparatus 12. Consequently, the biopsy apparatus 10 can easily be incorporated in existing mammographic apparatus.

The radiation source 26 moves in the X-Z plane, which extends transversely along the chest wall 52 of the examinee 20, i.e., in directions indicated by the arrow X, and also along the direction in which the breast 22 is compressed, i.e., in directions indicated by the arrow Z. The radiation source 26 applies radiation 24 to the breast 22 from a position at which the radiation source 26 has been moved and turned. The biopsy needle 64 is turned in the Y-Z plane along the direction in which the breast 22 is compressed, and across the plane in which the radiation source 26 is turned.

Since the plane along which the radiation source 26 is moved and the plane along which the biopsy needle 64 is turned differ from each other, the aforementioned advantages of the present embodiment can be achieved.

First and second modifications of the present invention will be described below with reference to FIGS. 19 through 21B.

Figure 19:
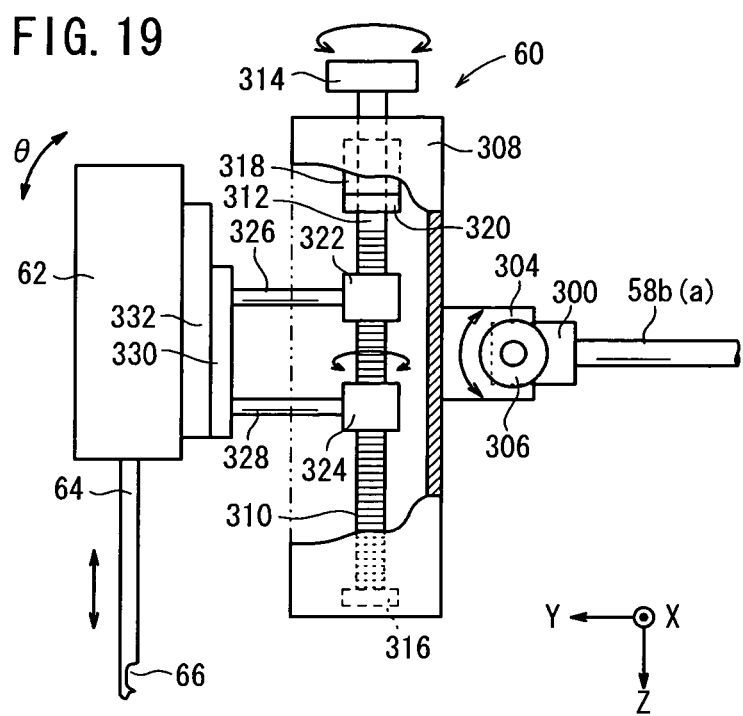
FIG. 19 is a side elevational view, partially cut away, of a biopsy apparatus according to a first modification of the present invention.

According to the first modification shown in FIG. 19, the biopsy needle holder 60 includes a function to turn in directions indicated by the arrow θ, as well as a function to move in directions indicated by the arrow Z.

More specifically, a mount 300 supported on distal ends of the rods 58a, 58b pivotally supports a turning member 304 through a handle 306, an axis of which extends along directions indicated by the arrow X. A hollow movable casing (reference position changer) 308 is mounted on the turning member 304.

A rotational shaft 312 that extends in directions indicated by the arrow Z is housed in the movable casing 308. The rotational shaft 312 has one end that extends through an end wall of the movable casing 308 and which is coupled to a handle 314, and another end rotatably supported by a bearing 316 on the other end wall of the movable casing 308. The rotational shaft 312 is connected to and extends through a motor 318 and a rotary encoder 320 within the movable casing 308 near the handle 314. The rotational shaft 312 has an externally threaded portion 310 extending axially between the rotary encoder 320 and the bearing 316.

Sliders 322, 324 are threaded over the externally threaded portion 310 for movement along directions indicated by the arrow Z. A mount 330 is connected to the sliders 322, 324 by respective joints 326, 328, which are coupled to the sliders 322, 324. The biopsy needle support 62 is mounted on the mount 330 through an attachment 332.

When a doctor or radiological technician turns the handle 306, the turning member 304 is turned in directions indicated by the arrow θ. Therefore, the movable casing 308 that is coupled to the turning member 304, the joints 326, 328, the mount 330, the attachment 332, the biopsy needle support 62, and the biopsy needle 64 also are turned together in unison in directions indicated by the arrow θ.

When a doctor or radiological technician turns the handle 314, or when the motor 318 is energized, the rotational shaft 312 is turned about its axis. The sliders 322, 324 move vertically along the rotational shaft 312 by converting rotation of the rotational shaft 312 into linear movement in directions indicated by the arrow Z. The mount 330 that is coupled to the sliders 322, 324, the attachment 332, the biopsy needle support 62, and the biopsy needle 64 also are moved together in unison vertically along the rotational shaft 312 in directions indicated by the arrow Z.

When the biopsy needle moving mechanism 56 is turned as a whole in directions indicated by the arrow θ, the distance between the biopsy region 36 and the tip end of the biopsy needle 64 may be increased (see FIG. 15). According to the first modification shown in FIG. 15, the sliders 322, 324 are moved vertically along the rotational shaft 312 in order to bring the tip end (reference position) of the biopsy needle 64 toward the biopsy region 36. In this manner, an increase in the distance that the biopsy needle 64 moves is canceled, and hence the biopsy apparatus 10 can be prevented from increasing in size.

Figure 20A:
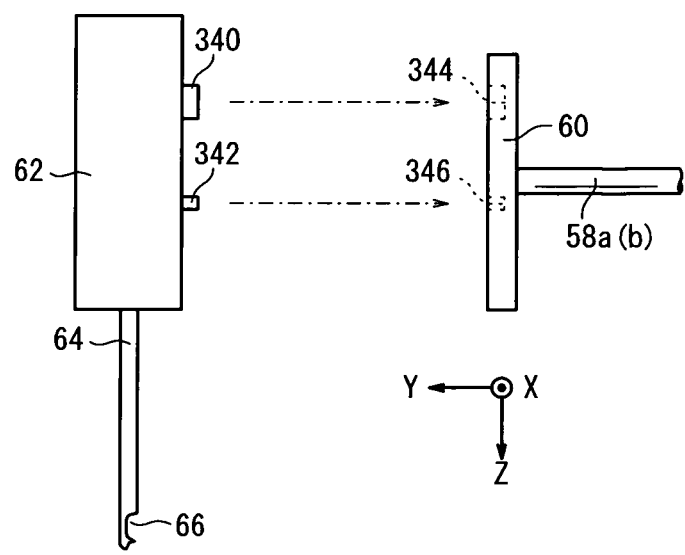
FIGS. 20A and 20B are side elevational views of a biopsy apparatus according to a second modification of the present invention.

According to the second modification shown in FIGS. 20A through 21B, the biopsy needle holder 60 has recesses or holes (reference position changer) 344, 346 defined in one surface thereof remote from the rods 58a, 58b and having different diameters, respectively. The biopsy needle support 62 has bosses (reference position changer) 340, 342, which are sized to fit respectively into the recesses 344, 346. The bosses 340, 342 shown in FIGS. 20A and 20B are different in position from the bosses 340, 342 shown in FIGS. 21A and 21B.

Figure 20B:
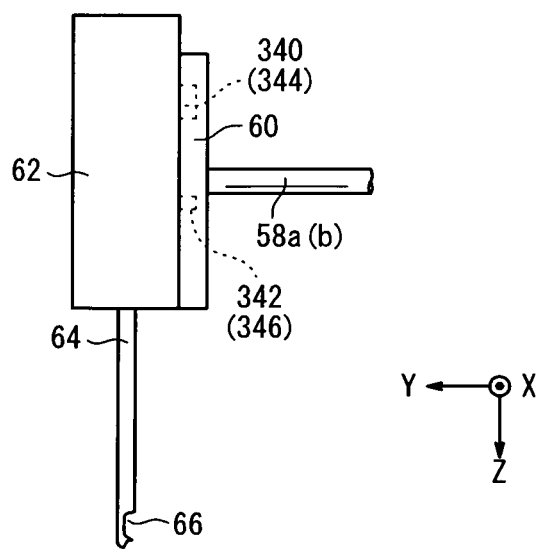
Figure 21A:
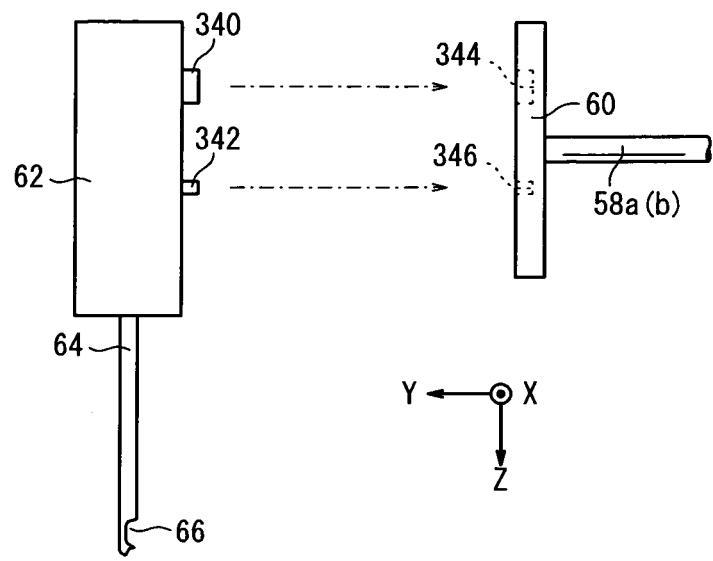
FIGS. 21A and 21B are side elevational views of a biopsy apparatus according to the second modification of the present invention.
Figure 21B:
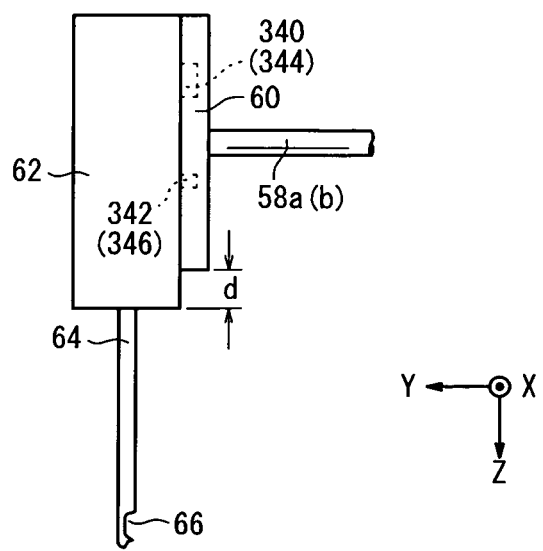

When the biopsy needle moving mechanism 56 is turned as a whole in directions indicated by the arrow θ, the distance between the biopsy region 36 and the tip end of the biopsy needle 64 is increased (see FIG. 15). According to the second modification, the biopsy needle support 62 shown in FIGS. 20A and 20B is removed from the biopsy needle holder 60, and the biopsy needle support 62 shown in FIGS. 21A and 21B is installed on the biopsy needle holder 60, thereby bringing the tip end (reference position) of the biopsy needle 64 toward the biopsy region 36, i.e., moving the tip end of the biopsy needle 64 by a distance d (see FIG. 21B), in order to compensate for the increase in the distance between the biopsy region 36 and the tip end of the biopsy needle 64. In this manner, the increase in distance that the biopsy needle 64 has moved is canceled, and hence the biopsy apparatus 10 can be prevented from increasing in size. Since the bosses 340, 342 and the recesses 344, 346 have different sizes, the bosses 340, 342 and the recesses 344, 346 prevent a doctor or radiological technician from mistakenly installing an incorrect one of the biopsy needle supports 62 on the biopsy needle holder 60.

Although certain preferred embodiments of the present invention have been shown and described in detail, it should be understood that various changes and modifications may be made to the embodiments without departing from the scope of the invention as set forth in the appended claims.

What is claimed is:

1. A biopsy apparatus for use in a mammographic apparatus having an image capturing base for holding a breast of a subject thereon, a compression plate displaceable toward the image capturing base for compressing the breast, a radiation source for applying radiation to the breast compressed, and a radiation detector contained in the image capturing base for detecting radiation that has passed through the breast and converting the detected radiation into a radiographic image, the biopsy apparatus being arranged so as to insert a biopsy needle into a biopsy region of the breast and sample tissue from the biopsy region, the biopsy apparatus comprising:

- a biopsy region positional information calculator configured to calculate a three-dimensional position of the biopsy region based on at least two radiographic images acquired from the radiation detector when the radiation is applied in different directions to the breast from the radiation source;
- a biopsy needle moving mechanism configured to move the biopsy needle along three mutually perpendicular axes and/or configured to turn the biopsy needle obliquely with respect to the breast;
- a biopsy needle positional information calculator configured to calculate a three-dimensional position of the biopsy needle;
- a compression plate positional information calculator configured to calculate a position of the compression plate with respect to the image capturing base, the position of the compression plate representing thickness information of the breast compressed; and
- a traveled distance calculator configured to determine that the biopsy needle pierces the breast according to an oblique piercing process or a vertical piercing process, based on the position of the compression plate, and configured to calculate a distance over which the biopsy needle moves with respect to the biopsy region in the determined piercing process based on the three-dimensional position of the biopsy needle and the three-dimensional position of the biopsy region,
- wherein the biopsy needle moving mechanism is configured to determine whether to turn the biopsy needle or not based on the position of the compression plate, and
- wherein on condition that the biopsy needle moving mechanism turns the biopsy needle, the biopsy needle positional information calculator is configured to calculate the three-dimensional position of the biopsy needle based on a turning angle of the biopsy needle.

2. A biopsy apparatus according to claim 1, wherein the biopsy needle moving mechanism comprises:
- a biopsy needle holder for holding the biopsy needle;
- at least two moving units for moving the biopsy needle holder along the three axes; and
- a turning unit configured to turn the biopsy needle holder obliquely with respect to the breast,
- wherein on condition that the turning unit does not turn the biopsy needle, the travel distance calculator is configured to calculate a difference between the three-dimensional position of the biopsy region and the three-dimensional position of the biopsy needle that is not turned, and is configured to determine the difference as the distance over which the biopsy needle moves, and
- wherein on condition that the turning unit turns the biopsy needle, the biopsy needle positional information calculator is configured to renew the three-dimensional position of the biopsy needle by calculating a three-dimensional position of the biopsy needle that is turned, after calculating the three-dimensional position of the biopsy needle that is not turned, and the travel distance calculator is configured to calculate a difference between the three-dimensional position of the biopsy region and the calculated three-dimensional position of the biopsy needle, and is configured to determine the difference as the distance over which the biopsy needle moves.

3. A biopsy apparatus according to claim 2, wherein the biopsy needle moving mechanism further comprises:
- at least three displacement detectors for detecting displacements respectively along the three axes of the biopsy needle holder that is moved by the moving units and outputting the detected displacements to the biopsy needle positional information calculator; and
- an angle detector for detecting an angular displacement of the biopsy needle holder that is turned by the turning unit and outputting the detected angular displacement to the biopsy needle positional information calculator,
- wherein the biopsy needle positional information calculator is configured to calculate a three-dimensional position of the biopsy needle before being turned based on the detected displacements, and is configured to calculate a three-dimensional position of the biopsy needle after being turned based on the angular displacement.

4. A biopsy apparatus according to claim 3, wherein the biopsy needle moving mechanism further comprises:
- a base that is placed on the mammographic apparatus when the biopsy needle moving mechanism is incorporated in the mammographic apparatus,
- wherein the turning unit is configured to turn the biopsy needle moving mechanism as a whole with respect to the base, thereby turning the biopsy needle holder.

5. A biopsy apparatus according to claim 3, wherein the biopsy needle moving mechanism further comprises:
- a reference position changer for changing a reference position for the biopsy needle when the biopsy needle holder holds the biopsy needle.

6. A biopsy apparatus according to claim 5, further comprising:
- a biopsy needle support for supporting the biopsy needle thereon, the biopsy needle support being held by the biopsy needle holder,
- wherein while the biopsy needle support is held by the biopsy needle holder, the reference position changer is configured to change the reference position by changing the position of the biopsy needle support with respect to the biopsy needle holder, or by replacing the biopsy needle support, which is currently held by the biopsy needle holder, with another biopsy needle support that is held at a different position by the biopsy needle holder.

7. A biopsy apparatus according to claim 3, wherein the traveled distance calculator is configured to calculate an actual distance over which the biopsy needle moving mechanism has moved and/or turned the biopsy needle holder based on the distance which is output to the biopsy needle moving mechanism; and
- if the traveled distance calculator makes a judgment indicating that the biopsy needle moving mechanism has not moved and/or turned the biopsy needle holder based on the distance output to the biopsy needle moving mechanism, based on the difference between the distance output to the biopsy needle moving mechanism and the actual distance calculated by the traveled distance calculator, the traveled distance calculator is configured to output the judgment to an external circuit.

8. A biopsy apparatus according to claim 3, wherein the biopsy needle moving mechanism further comprises:
- an attachment by which the biopsy needle moving mechanism is removably attached to the mammographic apparatus.

9. A biopsy apparatus according to claim 3, wherein the three axes represent a direction in which the compression plate compresses the breast, and two axial directions perpendicular to the direction in which the compression plate compresses the breast; and on condition that the radiation source moves along a plane that extends transversely across a chest wall of the subject and along the direction in which the compression plate compresses the breast, and thereafter applies radiation to the breast, the turning unit is configured to turn the biopsy needle holder along a plane that lies along the direction in which the compression plate compresses the breast and across a plane in which the radiation source moves.

10. A biopsy apparatus according to claim 1, wherein the biopsy needle moving mechanism is configured to turn the biopsy needle obliquely in a vertical plane that extends in a front-rear direction of the breast.

\* \* \* \* \*